US009061988B2

(12) United States Patent
Welker-Nieuwoudt et al.

(10) Patent No.: US 9,061,988 B2
(45) Date of Patent: Jun. 23, 2015

(54) PROCESS FOR PRODUCING A CATALYTICALLY ACTIVE COMPOSITION BEING A MIXTURE OF A MULTIELEMENT OXIDE COMPRISING THE ELEMENTS MO AND V AND AT LEAST ONE OXIDE OF MOLYBDENUM

(71) Applicant: BASF SE, Ludwigshafen (DE)

(72) Inventors: Cathrin Alexandra Welker-Nieuwoudt, Birkenheide (DE); Cornelia Katharina Dobner, Ludwigshafen (DE); Christian Walsdorff, Ludwigshafen (DE); Klaus Joachim Mueller-Engel, Stutensee (DE); Josef Macht, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/170,816

(22) Filed: Feb. 3, 2014

(65) Prior Publication Data

US 2014/0221683 A1 Aug. 7, 2014

Related U.S. Application Data

(60) Provisional application No. 61/761,812, filed on Feb. 7, 2013.

(30) Foreign Application Priority Data

Feb. 7, 2013 (DE) .................... 10 2013 202 048

(51) Int. Cl.
*C07C 51/25* (2006.01)
*B01J 23/888* (2006.01)
*B01J 23/00* (2006.01)
*B01J 35/02* (2006.01)
*B01J 35/10* (2006.01)
*B01J 37/00* (2006.01)
*B01J 37/04* (2006.01)
*B01J 35/00* (2006.01)
*B01J 23/28* (2006.01)
*B01J 23/30* (2006.01)
*B01J 37/08* (2006.01)
*B01J 37/02* (2006.01)

(52) U.S. Cl.
CPC ............. *C07C 51/252* (2013.01); *B01J 23/002* (2013.01); *B01J 23/8885* (2013.01); *B01J 35/023* (2013.01); *B01J 35/1009* (2013.01); *B01J 35/1014* (2013.01); *B01J 37/0045* (2013.01); *B01J 2523/00* (2013.01); *B01J 37/04* (2013.01); *B01J 37/08* (2013.01); *B01J 35/0006* (2013.01); *B01J 37/0219* (2013.01); *B01J 23/28* (2013.01); *B01J 23/30* (2013.01); *B01J 37/0036* (2013.01); *B01J 37/0221* (2013.01)

(58) Field of Classification Search
CPC ..... C07C 51/252; B01J 23/002; B01J 23/8885
USPC ........................................................ 562/535
See application file for complete search history.

(56) References Cited

U.S. PATENT DOCUMENTS

| | | | |
|---|---|---|---|
| 3,147,084 A | 9/1964 | Franzen et al. | |
| 7,589,046 B2 * | 9/2009 | Dieterle et al. | 502/311 |
| 2006/0205978 A1 | 9/2006 | Yunoki et al. | |
| 2008/0214863 A1 * | 9/2008 | Cremer et al. | 562/535 |

FOREIGN PATENT DOCUMENTS

| | | |
|---|---|---|
| DE | 2 201 428 A1 | 7/1973 |
| DE | 25 13 405 C2 | 10/1976 |
| DE | 28 30 765 A1 | 1/1980 |
| DE | 29 09 671 A1 | 10/1980 |
| DE | 199 10 506 A1 | 9/2000 |
| DE | 199 10 508 A1 | 9/2000 |
| DE | 199 27 624 A1 | 12/2000 |
| DE | 199 48 241 A1 | 4/2001 |
| DE | 199 48 523 A1 | 4/2001 |
| DE | 199 52 964 A1 | 5/2001 |
| DE | 100 51 419 A1 | 4/2002 |
| DE | 103 60 057 A1 | 7/2004 |
| DE | 103 60 058 A1 | 7/2004 |
| DE | 103 13 208 A1 | 10/2004 |
| DE | 10 2004 025 445 A1 | 2/2005 |
| DE | 103 50 822 A1 | 6/2005 |
| DE | 103 61 456 A1 | 7/2005 |
| DE | 10 2005 010 645 A1 | 8/2005 |
| DE | 10 2004 017150 A1 | 10/2005 |
| DE | 10 2007 019 597 A1 | 5/2008 |
| DE | 10 2008 040 093 A1 | 12/2008 |
| DE | 10 2008 040 094 A1 | 1/2009 |
| DE | 10 2008 054 586 A1 | 6/2010 |
| DE | 10 2010 028 328 A1 | 11/2011 |

(Continued)

OTHER PUBLICATIONS

U.S. Appl. No. 14/277,384, filed May 14, 2014, Gruene, et al.
International Search Report issued May 13, 2014 in PCT/EP2014/051556 filed Jan. 28, 2014 with English translation of categories of cited documents.
U.S. Appl. No. 14/535,743, filed Nov. 7, 2014, Macht, et al.
U.S. Appl. No. 14/536,969, filed Nov. 10, 2014, Macht, et al.

*Primary Examiner* — Yong Chu
(74) *Attorney, Agent, or Firm* — Oblon, McClelland, Maier & Neustadt, L.L.P.

(57) ABSTRACT

A process for producing a catalytically active composition being a mixture of a multielement oxide comprising the elements Mo and V and at least one oxide of molybdenum, in which spray drying of an aqueous solution or of an aqueous suspension of starting compounds comprising the elements of the multielement oxide produces a spray powder P, a pulverulent oxide of molybdenum and optionally shaping assistants are added thereto, shaped bodies are shaped from the resulting mixture and these are converted to the catalytically active composition by thermal treatment.

22 Claims, 12 Drawing Sheets

(56) References Cited

FOREIGN PATENT DOCUMENTS

| | | |
|---|---|---|
| DE | 10 2011 084 040 A1 | 1/2012 |
| DE | 10 2012 207 811 A1 | 7/2012 |
| EP | 0 383 224 A2 | 8/1990 |
| EP | 0 468 290 A1 | 1/1992 |
| EP | 0 614 872 A1 | 9/1994 |
| EP | 0 700 174 A1 | 3/1996 |
| EP | 0 700 893 A1 | 3/1996 |
| EP | 0 714 700 A2 | 6/1996 |
| EP | 0 724 481 A1 | 8/1996 |
| EP | 0 990 636 A1 | 4/2000 |
| EP | 1 106 598 A2 | 6/2001 |
| JP | 58-096041 A | 6/1983 |
| JP | 2007-260588 A | 10/2007 |
| JP | 2010-155197 A | 7/2010 |
| WO | WO 95/11081 A1 | 4/1995 |
| WO | WO 02/24327 A1 | 3/2002 |
| WO | WO 2004/085365 A2 | 10/2004 |
| WO | WO 2004/085367 A1 | 10/2004 |
| WO | WO 2004/085368 A2 | 10/2004 |
| WO | WO 2004/085369 A1 | 10/2004 |
| WO | WO 2004/085370 A1 | 10/2004 |
| WO | WO 2004/108267 A1 | 12/2004 |
| WO | WO 2004/108284 A1 | 12/2004 |
| WO | WO 2005/016861 A1 | 2/2005 |
| WO | WO 2005/042459 A1 | 5/2005 |
| WO | WO 2005/047226 A1 | 5/2005 |
| WO | WO 2005/120702 A1 | 12/2005 |
| WO | WO 2006/094766 A1 | 9/2006 |
| WO | WO 2006/114428 A1 | 11/2006 |
| WO | WO 2007/082827 A1 | 7/2007 |
| WO | WO 2008/104577 A1 | 9/2008 |
| WO | WO 2009/048553 A2 | 4/2009 |
| WO | WO 2011/134932 A1 | 11/2011 |

* cited by examiner

PROCESS FOR PRODUCING A CATALYTICALLY ACTIVE COMPOSITION BEING A MIXTURE OF A MULTIELEMENT OXIDE COMPRISING THE ELEMENTS MO AND V AND AT LEAST ONE OXIDE OF MOLYBDENUM

The present invention relates to a process for producing a catalytically active composition being a mixture of a multielement oxide comprising the elements Mo and V and at least one oxide of molybdenum.

The present invention also relates to the catalytically active compositions obtainable in accordance with the invention, to the use thereof for the catalysis of the heterogeneously catalyzed partial gas phase oxidation of (meth)acrolein to (meth) acrylic acid and to the use thereof for production of eggshell catalysts particularly suitable for this catalysis.

Multielement oxides comprising Mo and V are known in the prior art (cf., for example, WO 2011/134932 A1, DE 102012207811 A1, WO 2004/108267 A1, WO 2004/108284 A1, EP 714700 A2, DE 102005010645 A1, WO 95/11081 A1, DE 10350822 A1, US 2006/0205978 A1 and DE 102004025445 A1).

They are especially suitable as catalytically active compositions for the catalysis of the heterogeneously catalyzed partial gas phase oxidation of acrolein to acrylic acid.

The expression "multielement oxide" expresses the fact that the catalytically active composition also comprises at least one further chemical element in addition to Mo, V and O (oxygen).

The molar proportion of the element Mo in the total amount of all elements other than oxygen in the catalytically active multielement oxide is generally 5 to 95 mol %, frequently 10 to 90 mol % and in many cases 15 to 85 mol % or 20 to 80 mol %. The molar ratio of Mo in such a catalytically active multielement oxide to V present in the same catalytically active multielement oxide (molar amount of Mo present/molar amount of V present) is typically 15:1 to 1:1, frequently 12:1 to 2:1.

The prior art also discloses that a process for heterogeneously catalyzed gas phase partial oxidation of acrolein to acrylic acid catalyzed by a multielement oxide comprising the elements Mo and V can be conducted essentially continuously over prolonged periods over one and the same multielement oxide (cf., for example, DE 10350822 A1 and DE 102004025445 A1).

However, the multielement oxide loses catalytic efficacy with increasing operating time. In particular, its activity deteriorates.

In order nevertheless to be able to conduct the partial oxidation process for a maximum duration over one and the same active composition, attempts are made in the prior art to counteract this aging process in a wide variety of different ways.

EP 990636 A1 (e.g. page 8, lines 13 to 15) and EP 1106598 A2 (e.g. page 13, lines 43 to 46) propose substantially compensating for the reduction in activity of the active composition by gradually increasing the reaction temperature over the course of the operating time, under otherwise substantially unchanged operating conditions, in order to essentially maintain the acrolein conversion in single pass of the reaction mixture through the catalyst bed.

A disadvantage of the procedure recommended in EP 990636 A1 and in EP 1106598 A2 is that, with increasing rise of the reaction temperature, the aging process of the active composition accelerates to an increasing degree (particular movement processes within the active composition which contribute to aging proceed, for example, increasingly rapidly).

On attainment of a maximum value of the reaction temperature, the spent multielement oxide catalyst finally has to be exchanged. However, a disadvantage of such an exchange is that it is comparatively costly and inconvenient. The process for acrylic acid preparation has to be interrupted for a prolonged period and the costs of multielement oxide production are likewise considerable.

What are desirable are therefore procedures which help to prolong the service life of the active composition in the reactor to a maximum extent.

DE 102004025445 A1 proposes, as a process for long-term operation of the heterogeneously catalyzed partial gas phase oxidation of acrolein to acrylic acid, counteracting the deactivation of the multielement oxide by increasing the working pressure in the gas phase to an increasing degree with increasing operating time of the active composition. A disadvantage of this procedure is that, with increasing working pressure in the heterogeneously catalyzed partial gas phase oxidation, elevated compressor outputs are required.

There have also already been proposals to increase both the reaction temperature and the working pressure with increasing operating time.

EP 614872 A1 proposes extending the service life of the multielement oxide by, after an operating time of the active composition of several years, which is accompanied by increases in the reaction temperature of 15° C. to 30° C. or more for the purpose of maintaining the acrolein conversion (based on a single reactor pass of the reaction gas mixture), stopping the partial oxidation process and, at elevated temperature, passing a regeneration gas mixture of oxygen, steam and inert gas over and through the active composition, and then continuing the partial oxidation at reduced reaction temperature (in this connection, "inert gases" in a gas mixture which is conducted through a catalyst bed under particular conditions shall be understood quite generally in this document to mean those gases which, in the course of passage of the gas mixture through the catalyst bed, remain unchanged to an extent of at least 95 mol %, preferably to an extent of at least 98 mol %, most preferably to an extent of at least 99 mol % or to an extent of at least 99.5 mol %, or to an extent of 100 mol %).

However, a disadvantage of the procedure of EP 614872 A1 is that, up to the time of stoppage of the process, the aging of the multielement oxide continues and is promoted uninhibited. Moreover, the irreversible aging component of the active composition is maintained unchanged in the regeneration.

DE 10350822 A1 attempts to at least partly remedy the disadvantages of EP 614872 A1 by also increasing the reaction temperature of the multielement oxide stepwise over the operating time to compensate for the deactivation of the multielement oxide, but stopping the partial oxidation every time this temperature increase approaches 8° C. to conduct a molecular oxygen-comprising gas over and through the multielement oxide in a regenerating manner. A disadvantage of the procedure of DE 10350822 A1 is, however, that every regeneration necessitates an interruption of the actual partial oxidation process and is likewise unable to heal irreversible aging components.

An additional disadvantage of all the prior art processes acknowledged above for extending the service life of a multielement oxide comprising the elements Mo and V used as a catalytically active composition for performance of a heterogeneously catalyzed partial oxidation of acrolein to acrylic acid is that none of them attempt to preventatively counteract the onset of deactivation of the multielement oxide, and they instead only set in when such a deactivation of the multielement oxide has already occurred, in order to counteract the adverse effect of such a deactivation.

WO 2008/104577 A1, in contrast, discloses a process which preventatively counteracts the deactivation of a multielement oxide comprising the elements Mo and V in the course of a heterogeneously catalyzed partial gas phase oxidation of acrolein to acrylic acid catalyzed by the multielement oxide (in other words, comparatively delays the onset of deactivation).

The characterizing feature of the process of WO 2008/104577 A1 is that a pulverulent oxide of molybdenum is added to a separately produced pulverulent multielement oxide comprising Mo and V (effectively as an Mo depot), and the resulting mixture is used as a catalytically active composition for the heterogeneously catalyzed partial gas phase oxidation of acrolein to acrylic acid (for example as a catalytically active shell applied to the surface of an inert geometric shaped support body with the aid of a liquid binder).

However, a disadvantage of the procedure of WO 2008/104577 A1 is that, when it is employed, the activity level established in particular, but also the resulting selectivity of acrylic acid formation, is not fully satisfactory.

Figure 1A:
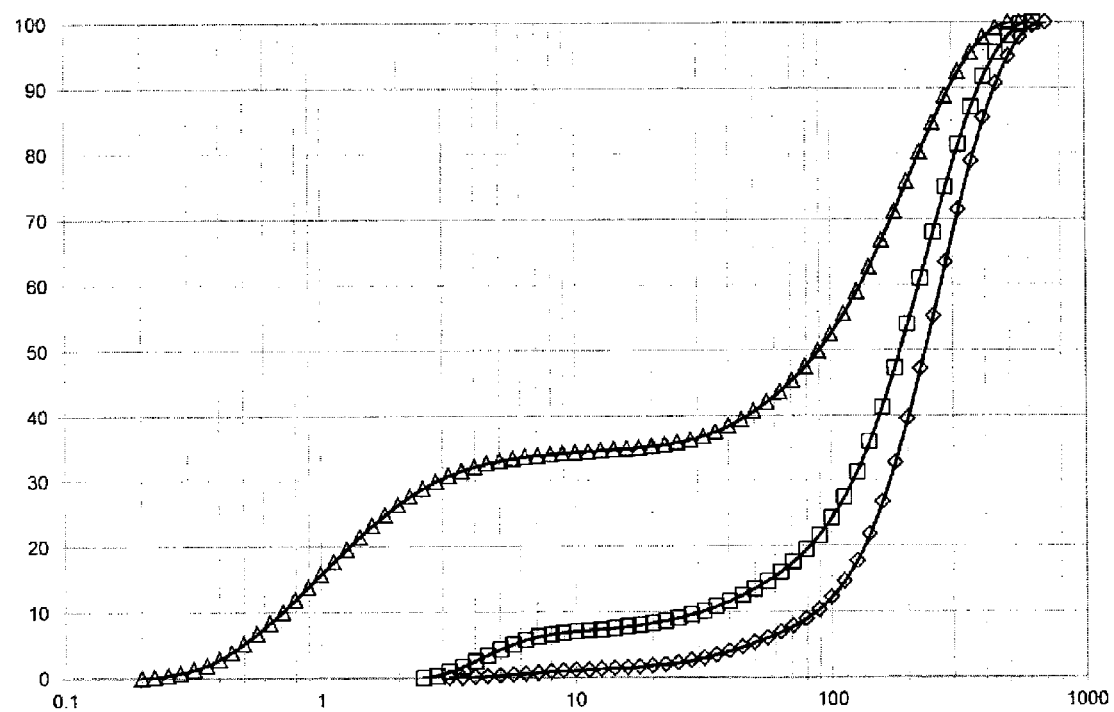
FIGS. 1a and 1b show particle diameter distributions of MoO3, determined to ISO 13320 as a function of the dispersion pressure employed in laser and Malvern.

It is a particular object of the present invention to provide an improved process for producing a catalytically active composition being a mixture of a multielement oxide comprising the elements Mo and V and at least one oxide of molybdenum, with the proviso that, firstly, the deactivation of the catalytically active composition obtainable (for example as an active composition shell of an eggshell catalyst, applied to the surface of a (preferably inert) geometric shaped support body), in the course of a heterogeneously catalyzed partial gas phase oxidation of acrolein to acrylic acid catalyzed thereby, sets in only in a comparatively retarded manner and, secondly, both the activity level exhibited and the selectivity of acrylic acid formation achieved are comparatively elevated.

Accordingly, a process for producing a catalytically active composition comprising a mixture of a multielement oxide comprising the elements Mo and V and at least one oxide of molybdenum is provided, which comprises the process measures of using sources of the elemental constituents of the multielement oxide to obtain an aqueous solution, or an aqueous suspension with the proviso that each of the sources passes through the state of an aqueous solution in the course of obtaining the aqueous suspension, spray drying the aqueous solution or aqueous suspension to obtain a spray powder P, using the spray powder P with addition of at least one pulverulent oxide S of molybdenum and optionally with addition of one or more shaping assistants and after homogeneous mixing of said constituents to form geometric shaped precursor bodies (geometric shaped bodies) using the resulting mixture, and thermally treating the geometric shaped precursor bodies to form the catalytically active composition.

An oxide of molybdenum is understood in this document, as in WO 2008/104577 A1, to mean a substance which, apart from any water of hydration present, which is not included here (not taken into account, neglected), consists only of Mo and O to an extent of $\geq 98\%$ by weight, preferably to an extent of $\geq 99\%$ by weight and more preferably to an extent of $\geq 99.5\%$ by weight or to an extent of $\geq 99.9\%$ by weight or more (it most preferably consists of 100% by weight of Mo and O). In other words, an oxide S of molybdenum usable in accordance with the invention, for example $MoO_2$, in spite of the stated stoichiometry "$MoO_2$", may comprise up to 2% of its weight of Mo and O and of constituents other than water. For the rest, the term "oxide S of molybdenum" in this document shall also include (comprise) hydrates of oxides of molybdenum, for example $MoO_3 \times H_2O$. These are frequently also formulated as hydroxides. Preferably in accordance with the invention, the oxide S of molybdenum, however, is free of water of hydration (in other words, the water content thereof is advantageously $\leq 2\%$ by weight based on the overall composition).

More preferably, the oxide S of molybdenum used for the process according to the invention will be molybdenum trioxide ($MoO_3$). In principle, however, examples of useful molybdenum oxides S suitable in accordance with the invention also include oxides such as the already mentioned $MoO_2$ or oxides such as $Mo_{18}O_{52}$, $Mo_8O_{23}$ and $Mo_4O_{11}$ (cf., for example, "Synthese und strukturelle Untersuchungen von Molybdän-, Vanadium- und Wolframoxiden als Referenzverbindungen für die heterogene Katalyse" [Synthesis and Structural Studies of Molybdenum Oxides, Vanadium Oxides and Tungsten Oxides as Reference Compounds for Heterogeneous Catalysis], Thesis by Dr. Andreas Blume, School II, Mathematics and Natural Sciences, of the Technische Universität Berlin, 2004, or Surface Science 292 (1983) 261-6, or J. Solid State Chem. 124 (1966) 104).

Appropriately for application purposes, the specific surface area $SA_M$ of a molybdenum oxide used in the process according to the invention as the pulverulent oxide S of molybdenum is, in accordance with the invention, preferably $\leq 20$ m$^2$/g, more preferably $\leq 15$ m$^2$/g and most preferably $\leq 10$ m$^2$/g. In general, the specific surface area $SA_M$ will, however, be $\geq 0.01$ m$^2$/g, frequently $\geq 0.05$ m$^2$/g and in many cases $\geq 0.1$ m$^2$/g or $\geq 0.5$ m$^2$/g or $\geq 1$ m$^2$/g (e.g. 5 m$^2$/g). The specific surface area, as always in this document (unless explicitly stated otherwise), is understood to mean the specific BET surface area (determined by gas adsorption ($N_2$) according to Brunauer-Emmett-Teller (BET)). A description of the BET determination method can be found in DIN ISO 9277 and in J. Am. Chem. Soc. Vol. 60, No. 2, pages 309-319 (1938).

The above statements relating to $SA_M$ apply especially when the pulverulent oxide S of molybdenum is pulverulent molybdenum trioxide $MoO_3$. The reason why a comparatively low value of $SA_M$ is advantageous is that a pulverulent molybdenum oxide S having a low value of $SA_M$, when used alone as the active composition for the corresponding heterogeneously catalyzed partial gas phase oxidation of acrolein to acrylic acid, is substantially inert, i.e. essentially does not cause any conversion of the acrolein.

Figure 1B:
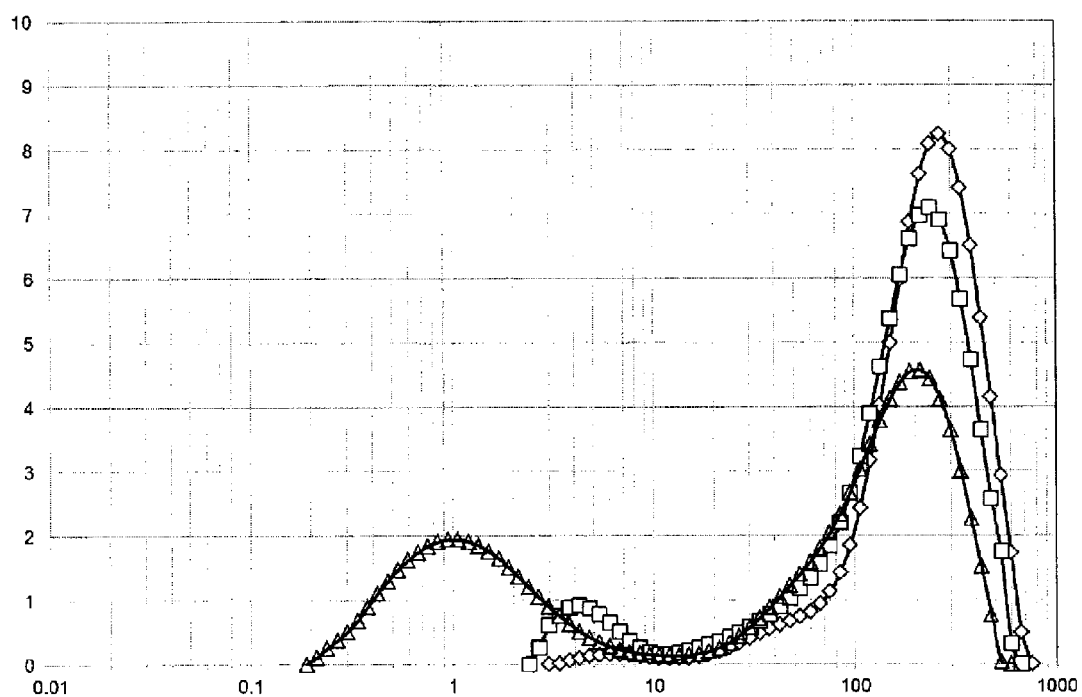

The granularity (particle diameter, or particle diameter distribution) of a molybdenum oxide used as the pulverulent oxide S of molybdenum in a process according to the invention is, advantageously in accordance with the invention, not coarser than that of the spray powder P produced in the same process according to the invention (this enables particularly homogeneous mixing of a pulverulent oxide S of molybdenum into a spray powder P). This is especially true when the pulverulent oxide S of molybdenum used in accordance with the invention is pulverulent molybdenum trioxide ($MoO_3$).

It will be appreciated that the granularity of a molybdenum oxide used as the pulverulent oxide S of molybdenum in a process according to the invention may also be coarser or finer than the granularity of the spray powder P produced in the same process according to the invention.

Particle diameter distributions and particle diameters $d_x$ (e.g. $d_{10}$, or $d_{50}$, or $d_{90}$) inferred from these relate in this document, unless explicitly stated otherwise, to determinations to ISO 13320 with the Malvern Mastersizer S laser diffraction spectrometer (Malvern Instruments, Worcestershire WR14 1AT, United Kingdom).

The particle diameters $d_x$ reported as the measurement result are defined such that X % of the total particle volume consists of particles having this or a smaller diameter.

To determine particle diameter distributions, the particular finely divided powder is, appropriately from an application point of view, conducted through a dispersing channel into the Sympatec RODOS dry disperser (Sympatec GmbH, System-Partikel-Technik, Am Pulverhaus 1, D-38678 Clausthal-Zellerfeld) and dry dispersed there with compressed air and blown into the measurement cell in a free jet. In this cell, the actual laser diffraction determination is then effected (unless explicitly stated otherwise in this document, the $d_x$ values reported are based on a determination of the particle diameter distribution at a dispersion pressure (=absolute pressure of the compressed air employed as propellant gas) of 2 bar abs.).

Typically, the particle diameters $d_{10}$ and $d_{90}$ of a spray powder P used in the process according to the invention are within the diameter range of 1 to 70 μm.

In the same way, the granularity of a pulverulent oxide S of molybdenum for additional use in accordance with the invention (especially when it is molybdenum trioxide ($MoO_3$)), in the process according to the invention, is typically such that its particle diameter $d_{90}$ is ≤20 μm, preferably ≤10 μm, more preferably ≤5 μm and most preferably ≤3 μm or ≤2 μm.

Normally, the particle diameter $d_{10}$ of a pulverulent oxide S of molybdenum for additional use in accordance with the invention (especially when it is molybdenum trioxide ($MoO_3$)) will, however, be ≥50 nm, preferably ≥75 nm, more preferably ≥100 nm, and most preferably ≥150 nm or ≥200 nm.

In other words, useful pulverulent oxides S of molybdenum for the process according to the invention (especially when they are molybdenum trioxide ($MoO_3$)) are those for which 50 nm $\leq d_{10}$; $d_{90} \leq 20$ μm, advantageously 75 nm$\leq d_{10}$); $d_{90} \leq 10$ μm, preferably 100 nm$\leq d_{10}$; $d_{90} \leq 5$ μm and more preferably 150 nm$\leq d_{10}$; $d_{90} \leq 3$ μm or 200 nm$\leq d_{10}$; $d_{90} \leq 2$ μm.

The total use amount of pulverulent oxide S of molybdenum (especially when it is molybdenum trioxide ($MoO_3$)) in a process according to the invention, based on the weight of the inventive catalytically active composition obtainable in this process, will, appropriately in application terms, be >0 and ≤50% by weight. Advantageously in accordance with the invention, the aforementioned total use amount, on the same basis, will be ≤45% by weight or ≤40% by weight. Preferably in accordance with the invention, the aforementioned total use amount on the same basis will be ≥1 and ≤35% by weight, more preferably ≥3 and ≤30% by weight and most preferably ≥5 and ≤30% by weight or ≥10 and ≤25% by weight, or ≥10 and ≤20% by weight (or ≤15% by weight).

The aforementioned total use amounts apply (like all other figures in this document) especially when the pulverulent oxide S of molybdenum is molybdenum trioxide ($MoO_3$).

In principle, a molybdenum oxide (e.g. $MoO_3$) suitable as the pulverulent oxide S of molybdenum for the process according to the invention can be obtained in a controlled manner from another substance comprising Mo.

For this purpose, it is possible to proceed, for example, from ammonium heptamolybdate tetrahydrate [$(NH_4)_6Mo_7O_{24} \times 4H_2O$]. For example, thermal treatment at 350° C. for 3 hours in an air stream likewise having a temperature of 350° C. converts it to $MoO_3$. Appropriate grinding and sieving can adjust the granularity of the $MoO_3$ in any desired manner as required. The specific surface area of the $MoO_3$ obtainable as described can likewise be adjusted as desired. With increasing duration of the thermal treatment and/or elevation of the temperature of the thermal treatment (on completion of $MoO_3$ formation under inert gas or under a gas atmosphere comprising molecular oxygen, for example air), the specific surface area decreases.

After formation of the $MoO_3$ at 350° C., undertaken as described above, thermal treatment at 550 to 650° C. for 4 to 8 hours in an air stream having an appropriate temperature is generally sufficient to suppress the specific surface area $SA_M$ of the $MoO_3$ to a value of ≤5 $m^2/g$ or of ≤2 $m^2/g$. Grinding can increase the specific surface area $SA_M$ of an $MoO_3$.

It will be appreciated that molybdenum oxides suitable as pulverulent oxide S of molybdenum for the process according to the invention can also be purchased commercially or prepared as required, proceeding from commercially available molybdenum oxides.

For example, the pulverulent oxide S of molybdenum used for the process according to the invention may be $MoO_3$ from Climax Molybdenum Marketing Corporation (Phoenix (Ariz.), USA), which has a molybdenum content of 66.60% by weight, a purity of ≥99.5% by weight and a specific surface area $SA_M$ of 3±1 $m^2/g$ (trade name: "pure Molybdenum Oxide Crystalline POC"), or, by means of processing thereof (for example the action of ultrasound and/or grinding), it is possible to obtain a molybdenum trioxide which is suitable in accordance with the invention as the pulverulent oxide S of molybdenum and has been modified in the desired manner.

FIGS. 1*a* and 1*b* of this document show, for this commercially available $MoO_3$, the particle diameter distributions determined to ISO 13320 as a function of the dispersion pressure employed in each case (laser, Malvern). In FIG. 1*a*, the abscissa shows the diameter [μm] on a logarithmic scale (to base 10) and the ordinate shows the proportion by volume of $MoO_3$ (in % by volume, based on the total particle volume) that has the respective particle diameter on the abscissa. In FIG. 1*b*, the abscissa, again in a logarithmic plot (on a logarithmic scale to base 10), shows the particle diameter (the particle dimension) in μm. The ordinate here, however, shows the proportion by volume of the total particle volume that has the respective diameter or a smaller diameter (dispersion pressures employed: ◇ =1.1 bar abs.; □=2 bar abs.; Δ=4.5 bar abs.).

The particles of this commercially purchasable $MoO_3$ are agglomerates of primary particles. The action of ultrasound, for example, can bring about the breakdown of the agglomerates to the smaller primary particles (cf. FIG. 1 of WO 2008/104577 A1). For an inventive use as the pulverulent oxide S of molybdenum, all particle diameter distributions obtainable by blending the two particle diameter distributions shown in FIG. 1 of WO 2008/104577 A1 (dispersion pressure: 2 bar abs.) are useful in principle (in any desired mass ratios; e.g. 1000:1 to 1:1000, or 100:1 to 1:100, or 10:1 to 1:10, or 5:1 to 1:5, or 2:1 to 1:2). In practice, these particle diameter distributions can be obtained, for example, by mixing primary particles and agglomerate with one another in the appropriate mass ratio.

Proceeding from the different particle diameter distributions above, grinding or grinding and sieving the corresponding pulverulent molybdenum trioxides can enhance the level of division (fineness) thereof as desired (the particle diameters can be reduced as appropriate). The extraneous constituent specification for the aforementioned $MoO_3$ is shown on page 8 of WO 2008/104577. It is of course also possible in accordance with the invention to use $MoO_3$ from the Climax Molybdenum Marketing Corporation of the "POS" type as the pulverulent oxide S of molybdenum.

Alternatively, the commercially purchasable $MoO_3$ used as the pulverulent oxide S of molybdenum may also be $MoO_3$ from H.C. Starck, D-38615 Goslar, through appropriate processing (for example grinding of the commercially purchasable product) (trade name: "Molybdenum Trioxide I"). This has a specific surface area $SA_M$ of 1 $m^2/g$. The molybdenum content of this $MoO_3$
is 66.6% by weight. The extraneous component specification of this $MoO_3$ is shown on page 9 of WO 2008/104577. The corresponding particle diameter distribution is shown in FIG. 2 of WO 2008/104577.

The $MoO_3$ particles of the above-described $MoO_3$ from H.C. Starck are likewise agglomerates of primary particles. In contrast to the $MoO_3$ particles of the above-described $MoO_3$ from Climax, however, the coherence of the primary particles is much less marked, and the applicant was therefore unable to bring about any breakdown into the primary particles by the action of ultrasound, for example. By grinding or grinding and sieving, however, the particle diameters can be reduced as required.

Of course, the pulverulent oxides S of molybdenum used in the process according to the invention may also be those based on molybdenum trioxides of the "II" types from H.C. Starck.

Incidentally, for the process according to the invention, it is also possible to use pulverulent oxide S of molybdenum based on $MoO_3$ from the following manufacturers:
  Metal-Tech.-Ltd. (Israel), purity>98% by weight, $SA_M$=1.1 $m^2/g$;
  Gulf Chemical (Texas, USA), 65.76% by weight Mo, $SA_M$=1.2 $m^2/g$;
  Nanjing Chemical Industries (China), 66.6% by weight Mo, $SA_M$=0.8 $m^2/g$;
  Kankal Exports (India), purity≥99% by weight, $SA_M$=1.7 $m^2/g$;
  Taiyo Koko Co., Ltd. (Japan), purity≥99.7% by weight, $SA_M$=1.6 $m^2/g$;
  Anhui Chizhou Huangshanling Lead and Zinc Mine (China), purity≥99.7% by weight, 66.5% by weight Mo, $SA_M$=0.3 $m^2/g$; and
  CCl Moly B.V. (the Netherlands), purity>99.5% by weight, >66% by weight Mo, $SA_M$=2.5 $m^2/g$.

Figure 2A:
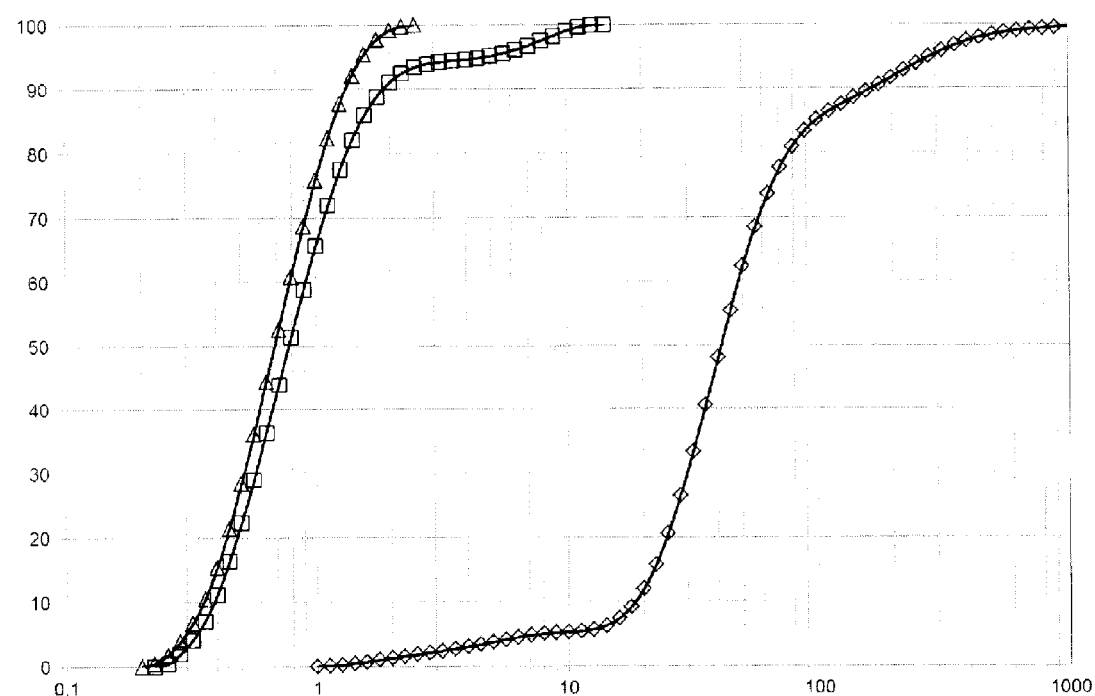
FIGS. 2a and 2b show particle diameter distributions of the pulverulent oxide S of molybdenum particularly suitable for the process according to the invention.
Figure 2B:
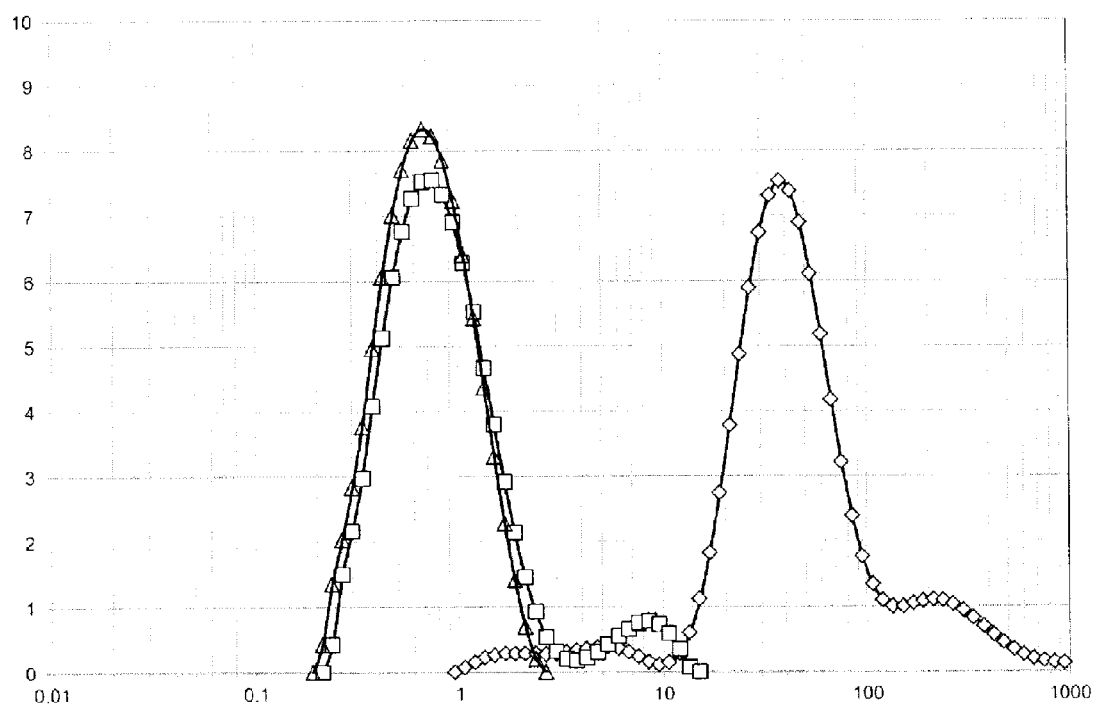

A particle diameter distribution of the pulverulent oxide S of molybdenum particularly suitable for the process according to the invention (especially when this is a molybdenum trioxide ($MoO_3$)) is shown in FIGS. 2a and 2b of this document (this is especially true when the pulverulent oxide S of molybdenum has been obtained by grinding "pure Molybdenum Oxide Crystalline POC" from Climax Molybdenum Marketing Corporation). In FIG. 2a, the abscissa shows the diameter [μm] on a logarithmic scale (to base 10) and the ordinate shows the proportion by volume (% by volume) of the total particle volume of the oxide S of molybdenum that has the respective diameter, as a function of the dispersion pressure employed. In FIG. 2b, the abscissa, again in a logarithmic plot (on a logarithmic scale to base 10), shows the particle diameter (the particle dimension) in μm. The ordinate here, however, shows the proportion by volume of the total particle volume that has the particular diameter or a smaller diameter. The determinations were effected as in the case of the particle diameter distributions shown in FIG. 1 (dispersion pressures employed:
  ◊=1.1 bar abs.; □=2 bar abs.;
  Δ=4.5 bar abs.).

To produce the spray powder P in the process according to the invention, suitable sources of the elemental constituents of the multielement oxide comprising the elements Mo and V are used to obtain an aqueous solution, or an aqueous suspension with the proviso that each of the sources passes through the state of an aqueous solution in the course of obtaining the aqueous suspension.

In other words, starting compounds (sources) comprising the elemental constituents other than oxygen in the contemplated multielement oxide as constituents are used to produce only one or more than one aqueous solution.

In the former case, the aqueous solution is directly that from which the powder P is obtained by spray drying. The amounts of the starting compounds (sources) present dissolved in such an aqueous solution are normally such that the aqueous solution comprises the relevant elemental constituents of the contemplated multielement oxide in molar ratios corresponding to the stoichiometry of this multielement oxide comprising Mo and V.

In the second case, when the starting compounds are used to obtain more than one aqueous solution (in which case a single aqueous solution may comprise only one or more than one starting compound (source) in dissolved form), the different aqueous solutions obtained are combined with one another, either forming an aqueous overall solution to be spray dried to give the spray powder P, or an aqueous suspension to be spray dried to give the spray powder P. The amounts of the starting compounds (sources) present dissolved in the aqueous overall solution, or of the constituents present dissolved and suspended in the aqueous suspension, are normally such that the aqueous overall solution or the aqueous suspension comprises the relevant elemental constituents of the contemplated multielement oxide in molar ratios corresponding to the stoichiometry of this multielement oxide comprising Mo and V.

In the inventive spray drying of the aqueous solution or aqueous suspension, the aqueous solution or aqueous suspension, appropriately in application terms, is introduced by means of a nozzle (operated by liquid pressure, compressed air or inert gas) or by means of rotating atomizer disks, divided into fine droplets, into a hot gas stream (preferably into a hot air stream) which dries it to a fine powder within fractions of a second. The hot gas stream (for example the hot air stream) can in principle flow in the direction of the spray jet (i.e. in cocurrent) or counter to the spray jet (i.e. in countercurrent). Favorably in application terms, cocurrent mode is preferred in accordance with the invention. Typical inlet temperatures of the hot gas stream (of the preferably hot air stream; in principle, however, it is also possible to use, for example, a hot nitrogen stream, a hot carbon dioxide stream or a hot noble gas stream) are 300 to 360° C., and typical exit temperatures are in the range from 100 to 150° C. The residual water content of the resulting spray powder (based on the total mass thereof), appropriately in accordance with the invention, is ≤10% by weight and particularly appropriately ≤6% by weight (low residual water contents are advantageous). In general, the aforementioned residual water content, pragmatically in application terms, is ≥0.5% by weight, frequently ≥2% by weight. Figures for residual water contents in this document are generally based on the determination thereof with the aid of the SMART System 5 microwave analysis system from CEM GmbH in D-47475 Kamp-Lintfort. Said system dries the sample to be analyzed by means of a focussed microwave (cf. also DE 102011084040 A1) on the balance incorporated into the measurement system. In the course of this, the analysis system permanently determines the weight loss (to constant weight) during the drying operation and downregulates the drying energy at the end point. A standard air flow duct integrated by the manufacturer into the microwave analysis system used continuously leads water vapor formed off and accelerates the drying operation. Any combustion or decomposition of the sample is prevented by temperature control (40° C. is not exceeded). The typical drying time of a 0.1 g sample is generally about 3 minutes.

The particle diameters of spray powders P for use in accordance with the invention are, according to the droplet division employed, appropriately in accordance with the invention, in the range from 1 μm to 50 μm. In general, spray powders P obtainable as described have comparatively homogeneous particle diameters.

On the way from the site of production thereof to the spray drying apparatus, the aqueous solution or aqueous suspension to be spray dried is passed through at least one filter, in order to remove any coarse particles present therein, which could, for example, block the spray nozzles, prior to the entry thereof into the spray drying apparatus. The temperature of the conveying line, appropriately in application terms, is kept at the final value of the production temperature of the aqueous solution or of the aqueous suspension. The residual solution or residual suspension which is yet to be spray dried in each case is advantageously mixed constantly by stirring and kept at the starting temperature relevant for the spray drying thereof.

In industry, the aqueous solution or aqueous suspension to be spray dried is normally produced in stirred vessels manufactured from stainless steel of the 1.4541 type (1.4541 material=AISI (American Iron and Steel Institute) 321). Appropriately in application terms, the spray drying apparatus and the stirrer are manufactured from the same material.

The molar proportion of the element Mo in the total amount of all elements other than oxygen in the multielement oxides comprising Mo and V which are advantageous for the process according to the invention is generally 5 to 95 mol %, frequently 10 to 90 mol % and in many cases 15 to 85 mol % or 20 to 80 mol %. The molar ratio of Mo to V in the multielement oxides comprising Mo and V favorable for the process according to the invention is generally 15:1 to 1:1, frequently 12:1 to 2:1.

As well as Mo, V and O, multielement oxides of good suitability in accordance with the invention frequently also comprise at least one of the elements Nb and W.

In many cases, the molar Mo/(total amount of W and Nb) ratio in such multielement oxides is in the range from 80:1 to 1:4. Frequently, such multielement oxides of good suitability for the process according to the invention additionally comprise Cu, preferably in a molar Mo/Cu ratio in the range from 30:1 to 1:3.

As well as the elements (elemental constituents) Nb and/or W and Mo, V and O and optionally Cu, multielement oxide compositions suitable for the process according to the invention may additionally comprise, for example, at least one of the elements (at least one of the elemental constituents) Ta, Cr, Ce, Ni, Co, Fe, Mn, Zn, Sb, Bi, alkali metals (Li, Na, K, Rb, Cs), H, alkaline earth metals (Mg, Ca, Sr, Ba), Si, Al, Ti and Zr.

Of course, a multielement oxide composition of good suitability for the process according to the invention may also consist only of the elements Nb and/or W, and Mo, V and O and optionally Cu.

Useful sources for the aforementioned elemental constituents (as starting compounds comprising at least one of the aforementioned elemental constituents) for production of the aqueous solutions or suspensions to be spray dried in the process according to the invention include both oxides of the elements and those compounds which comprise one or more than one relevant element and can be converted to oxides by heating, at least in the presence of oxygen. In addition to the oxides, useful starting compounds (element sources) are therefore in particular hydroxides, halides, nitrates, formates, oxalates, acetates, carbonates and/or hydrates thereof.

Starting compounds (sources) of the elemental multielement oxide constituents Mo, V, W and Nb suitable for the process according to the invention are also the oxo compounds thereof (molybdates, vanadates, tungstates and niobates) or the acids derived from these. Element sources comprising the element oxygen are generally favorable in the context of an inventive production of spray powder P.

If the solubility of a possible element source in aqueous medium is intrinsically inadequate for the purposes of the process according to the invention, it is possible, for example, to modify the pH of the aqueous medium by addition of appropriate modifiers, in order to improve the solubility of the element source in the aqueous medium. Suitable modifiers include particularly those Brønsted acids and Brønsted bases which decompose to gaseous constituents under the action of elevated temperatures, as employed in the thermal treatment of the geometric shaped precursor bodies to form the desired catalytically active composition. Examples of such pH modifiers include ammonia, nitric acid, hydrochloric acid, acetic acid, formic acid, oxalic acid and ammonium salts of strong and weak Brønsted acids, for example ammonium nitrate, ammonium chloride, ammonium carbonate, ammonium hydrogencarbonate, ammonium acetate, ammonium formate and ammonium oxalate.

Alternatively and/or additionally, complexing agents soluble in the aqueous medium can also be added thereto, these decomposing to gaseous compounds and/or escaping as gaseous compounds under the action of elevated temperatures (at least in the presence of molecular oxygen) and being able to complex elemental constituents present in ionic form in element sources, which generally likewise leads to an improvement in the solubility of the element source in the aqueous medium. Examples of such complexing agents include ammonia and ethylenediaminetetraacetic acid and salts thereof (preferably of good water solubility).

A further measure for improving the solubility of element sources in an aqueous medium is the employment of elevated temperatures. It is of course also possible, in the context of the inventive procedure, to simultaneously employ more than one of the various options addressed for improving the solubility of element sources in aqueous medium.

It is also possible to incorporate other organic and/or inorganic materials which escape in gaseous form and/or decompose to give gaseous constituents in the course of the inventive thermal treatment of the geometric shaped precursor bodies, for example stearic acid, malonic acid, ammonium salts of the aforementioned acids, starches (e.g. potato starch and/or corn starch), cellulose, ground nutshells and/or finely ground polymer (for example polyethylene, polypropylene etc.), into the aqueous solution or aqueous suspension to be spray dried in the process according to the invention to give the spray powder P (and hence into the geometric shaped precursor bodies to be treated thermally).

As is yet to be explained later in this patent application (and is known from the prior art in the context of production of customary multielement oxide active compositions comprising Mo and V), the inventive thermal treatment of the geometric shaped precursor bodies obtained in accordance with the invention to form the catalytically active compositions is advantageously effected in a gas atmosphere comprising $O_2$ and $NH_3$ (cf. WO 2008/104577 A1, WO 2004/108267 A1, EP 724481 A1 and WO 95/11081 A1). Advantageously in application terms, the $NH_3$ may evolve from the shaped precursor bodies themselves, by virtue of appropriate incorporation of a corresponding amount of ammonium ions therein.

Advantageously, the ammonium ions can be incorporated into the geometric shaped bodies to be thermally treated in accordance with the invention, for example, by using the corresponding ammonium oxometalates of such elements as sources of elements such as Mo, V, W or Nb in the course of production of the aqueous solution or aqueous suspension to be spray dried to give the spray powder P. Examples thereof are ammonium metaniobate, ammonium metavanadate, ammonium molybdate, ammonium heptamolybdate tetrahydrate and ammonium paratungstate heptahydrate. It is of course also possible to incorporate ammonium suppliers such as $NH_4NO_3$, or $NH_4Cl$, or ammonium acetate, or ammonium carbonate, or ammonium hydrogencarbonate, or $NH_4OH$, or $NH_4CHO_2$, or ammonium oxalate into the aqueous solution or aqueous suspension to be spray dried in the process according to the invention to give the spray powder P (and hence into the geometric shaped bodies to be treated thermally) independently of the starting compounds required as sources of the multielement oxide constituents.

Useful element compositions of a multielement oxide comprising Mo and V required for the process according to the invention are especially all stoichiometries which are known from the prior art for such multielement oxides and have been found to be particularly advantageous as active compositions for a catalytic partial oxidation of acrolein to acrylic acid.

These stoichiometries include particularly all of the stoichiometries (especially those detailed by way of example) disclosed in documents DE 10201002832 A1, DE 19927624 A1, WO 2011/134932 A1, WO 2008/104577 A1, DE 102012207811 A1, WO 2004/108267 A1, EP 724481 A1, WO 95/11081 A1, WO 2011/134932 A1, WO 2004/108284 A1, EP 714700 A2, DE 102005010645 A1, WO 95/11081 A1, DE 10350822 A1, US 2006/0205978 A1 and DE 102004025445 A1, and the prior art cited in these documents.

Some of these multielement oxide stoichiometries satisfy the following general stoichiometry (general formula) I $$Mo_{12}V_aX^1_bX^2_cX^3_dX^4_eX^5_fX^6_gO_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40, and
n=a number which is determined by the valency and frequency of the elements in I other than oxygen.

Among these multielement oxide stoichiometries of the general formula (I), for the process according to the invention, preference is given to those in which the variables are within the following ranges:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=2.5 to 5,
b=0.5 to 2,
c=0.5 to 3,
d=0 to 2,
e=0 to 0.2,
f=0 to 1,
g=0 to 15, and
n=a number which is determined by the valency and frequency of the elements in I other than oxygen.

Multielement oxide stoichiometries which are very particularly preferred in accordance with the invention satisfy the following general stoichiometry (general formula) II $$Mo_{12}V_aX^1_bX^2_cX^5_fX^6_gO_n \qquad (II)$$

in which the variables are each defined as follows:
$X^1$=W and/or Nb,
$X^2$=Cu and/or Ni,
$X^5$=Co and/or Sr,
$X^6$=Si and/or Al,
a=3 to 4.5,
b=1 to 1.5,
c=0.75 to 2.5,
f=0 to 0.5,
g=0 to 8, and
n=a number which is determined by the valency and frequency of the elements in II other than oxygen.

It should be emphasized here that multielement oxides suitable for the process according to the invention are also those which comprise, as elements other than oxygen, at least one of the two elements Te and Sb as well as the elements Mo and V, and at least one of the elements from the group consisting of Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination. From the latter element group, preference is given to the elements Nb, Ta, W and/or Ti, among which the element Nb is very particularly preferred (cf., for example, WO 2004/108267 A1 and WO 2008/104577 A1).

Preferred multielement oxide stoichiometries are those of the general stoichiometry III $$Mo_1V_bM^1_cM^2_d \qquad (III)$$

where

M¹=Te and/or Sb,

M²=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In, b=0.01 to 1, c=>0 to 1, and d=>0 to 1.

Preferably, M¹=Te and M²=Nb, Ta, W and/or Ti. Preferably, M²=Nb.

The stoichiometric coefficient b is advantageously 0.1 to 0.6.

In a corresponding manner, the preferred range for the stoichiometric coefficient c is 0.01 to 1 or 0.05 to 0.4, and favorable values for d are 0.01 to 1 or 0.1 to 0.6.

It is particularly favorable when the stoichiometric coefficients b, c and d are simultaneously within the aforementioned preferred ranges.

It should also be emphasized here that production of spray powders P suitable in accordance with the invention can be accomplished by employing all those procedures previously known from the prior art (especially the prior art acknowledged in this document) in the context of a production of multielement oxides comprising Mo and V.

To obtain the geometric shaped precursor bodies to be treated thermally in the process according to the invention (to form the catalytically active composition) from the spray powder P with addition of at least one oxide S of molybdenum, it is possible in accordance with the invention to follow different (various) process variants.

In a simple embodiment of the inventive procedure, the spray powder P and the at least one pulverulent oxide S of molybdenum are dry mixed with one another with maximum homogeneity (for example with the aid of a mixing apparatus). The resulting pulverulent mixture as such can subsequently be used directly to form geometric shaped bodies (geometric shaped precursor bodies) of any desired geometry by compaction (press agglomeration, tableting) (for example as shown by way of example in documents DE 102008054586 A1, DE 102008040093 A1 and DE 102008040094 A1 for comparable pulverulent mixtures). Examples of shaped precursor body geometries typical in accordance with the invention are, for example, spheres (the diameter of which may, for example, be 2 to 10 mm), and also solid cylinders or hollow cylinders (rings) having an external diameter and a length of typically 2 to 10 mm. In the case of the hollow cylinder, a wall thickness of 1 to 3 mm is appropriate.

It is of course also possible, in the course of mixing of spray powder P and at least one pulverulent oxide S of molybdenum, to additionally incorporate assistants for the subsequent shaping (shaping assistants) (before, during and/or after the mixing of spray powder P and at least one pulverulent oxide S of molybdenum).

Useful examples of these include glidants and lubricants such as graphite, carbon black, polyethylene glycol, stearic acid, salts of stearic acid, starch, polyacrylic acid, mineral oil, vegetable oil, water, boron nitride, boron trifluoride, glycerol, fine Teflon powder and/or cellulose ether.

The aforementioned lubricants may partly or fully decompose and/or be chemically converted in the course of the inventive thermal treatment of the geometric shaped precursor bodies, possibly to form substances which escape in gaseous form.

As further shaping assistants, the mixture to be compacted may comprise added reinforcing agents, which promote coherence in the resulting geometric shaped precursor bodies. Such reinforcing agents may, for example, be microfibers of glass, asbestos, silicon carbide and/or potassium titanate.

In contrast to the lubricants, reinforcing assistants are normally essentially completely preserved in the course of the inventive thermal treatment of the geometric shaped precursor bodies.

It is of course also possible to incorporate lubricants and reinforcing agents together in the course of mixing of spray powder P and at least one pulverulent oxide S of molybdenum.

Based on the total amount of a pulverulent mixture to be compacted in accordance with the invention to shaped precursor bodies, the total amount of shaping assistants present will generally not be more than 30% by weight, usually not more than 20% by weight and in many cases not more than 10% by weight (but frequently ≥0.1% by weight, or ≥0.2% by weight, or ≥0.5% by weight, or ≥1% by weight).

If the shaping in the course of the inventive production of the geometric shaped precursor bodies is effected by extrusion, it is advantageous in accordance with the invention to also incorporate at least one liquid (a liquid binder) as a shaping assistant in the course of mixing of spray powder P and at least one pulverulent oxide S of molybdenum. This liquid is preferably water, an aqueous solution and/or constituents of an aqueous solution. Advantageously in accordance with the invention, at least one aforementioned liquid shaping assistant incorporated is a lower ($C_2$ to $C_5$) organic carboxylic acid (e.g. formic acid, acetic acid (preferred), propionic acid, fumaric acid and/or maleic acid or the respective aqueous solution thereof and/or the constituents of such an aqueous solution).

Calculated as pure lower organic carboxylic acids, these (preferably acetic acid) are, advantageously in accordance with the invention, incorporated overall in a total amount of 5 to 10% by weight, based on the content of spray powder P in the overall mixture. The total water content of the resulting overall mixture may, for example, be 5 to 40% by weight, preferably 10 to 30% by weight.

The incorporation of one or more lower organic carboxylic acids (preferably acetic acid) and/or aqueous solutions thereof, appropriately in application terms, is effected by kneading with maximum homogeneity. The temperature in the course of kneading will generally not be more than 50° C. Typically, the aforementioned temperature is in the range from 20 to 50° C., appropriately in the range from 30 to 40° C.

The resulting viscous (slurrylike) composition (the resulting kneading material, the resulting kneading composition) is subsequently shaped by extrusion to shaped bodies (shaped precursor bodies) of the desired geometry. In the simplest case, these may be strands (solid cylinders). Of course, rings are also possible extrudates in accordance with the invention.

In the case of geometric shaped (precursor) bodies obtained by extrusion, an inventive thermal treatment thereof includes the drying thereof. In general, this drying is effected at temperatures <200° C., preferably ≤150° C., but typically at temperatures ≥30° C., or ≥40° C., or ≥50° C.

In addition, the inventive thermal treatment of the geometric shaped precursor bodies to form the catalytically active composition comprises (includes) such a drying operation (also referred to as calcination) at temperatures of 200 to 600° C., preferably of 300 to 450° C. or 300 to 400° C. (each material temperature). Especially during the calcination, the material, advantageously in accordance with the invention, has a very substantially uniform temperature.

The thermal treatment (especially the calcination) of the geometric shaped precursor bodies can be performed either under (in) inert gas or under (in) an oxidative (gas) atmosphere, for example air (or another mixture of inert gas and oxygen), or else under a reducing atmosphere (for example mixtures of inert gas and reducing gases such as $H_2$, $NH_3$, CO, methane and/or acrolein or said reducing gases alone) (it will be appreciated that an atmosphere having reducing action overall may also have a limited content of molecular oxygen). The inventive thermal treatment can in principle also be effected under reduced pressure.

If the inventive thermal treatment of the geometric shaped precursor bodies is effected under gaseous atmosphere, this may either be stationary or flowing. Overall, the inventive thermal treatment (especially the calcination) of the geometric shaped (precursor) bodies may take up to 24 h or more. Frequently, the thermal treatment (especially the calcination) of geometric shaped precursor bodies extends over a period of minutes to a few hours, for example from 0.5 h to 10 h, or from 1 h to 5 h. Elevated temperatures are normally associated with shorter durations of the thermal treatment (especially of the calcination) and, at lower temperatures, generally longer durations of the thermal treatment (especially of the calcination) are employed. High temperatures and long treatment times (especially of the calcination) generally reduce the specific surface area of the catalytically active multimetal oxide composition which results in the course of thermal treatment of the geometric shaped precursor bodies (of the precursor composition).

Appropriately in accordance with the invention, the particles of the at least one pulverulent oxide S of molybdenum present in the geometric shaped precursor bodies are preserved essentially unchanged in the course of the inventive thermal treatment, i.e. as regions delimited on the basis of their specific chemical composition.

The specific BET surface area $SA_A$ ($m^2/g$) of the catalytically active compositions obtainable in accordance with the invention (of the calcined geometric shaped precursor bodies (treated thermally in accordance with the invention)) is, appropriately in application terms, 5 to 40 $m^2/g$, advantageously 10 to 30 $m^2/g$ and preferably 10 to 20 $m^2/g$ (e.g. 15 $m^2/g$).

The inventive thermal treatment (especially the calcination) of the geometric shaped precursor bodies is preferably effected in a gas atmosphere comprising $O_2$ and $NH_3$.

The $NH_3$ may evolve from the shaped precursor bodies themselves by virtue of an appropriate amount of ammonium ions being incorporated into it.

The resulting catalytic activity of the catalytically active composition obtained in the inventive thermal treatment generally exhibits an optimum depending on the oxygen content of the calcination atmosphere.

Preferably, the oxygen content (the content of molecular oxygen) in the calcination atmosphere is 0.5 to 10% by volume, more preferably 1 to 5% by volume. Oxygen contents above and below the aforementioned limits normally reduce the resulting catalytic activity.

Calcination processes suitable in accordance with the invention are disclosed, for example, by the documents WO 2004/108284 A1, EP 724481 A1, WO 2008/104577 A1, WO 2004/108267 A1 and WO 95/11081 A1, among which the calcination process disclosed in the latter WO document is especially preferred in accordance with the invention.

The geometric shaped catalyst bodies which are obtained (are the result) within an inventive thermal treatment of geometric shaped precursor bodies can be used as such (as what are called unsupported catalysts) in the fixed catalyst bed for catalysis of the heterogeneously catalyzed partial gas phase oxidation of acrolein to acrylic acid.

Unsupported catalyst geometries suitable in accordance with the invention are, for example, solid cylinders or hollow cylinders having an external diameter and a length of 2 to 10 mm. In the case of the hollow cylinder, a wall thickness of 1 to 3 mm is appropriate. The unsupported catalyst may of course also have spherical geometry, in which case the sphere diameter may be 2 to 10 mm.

It is also possible for the geometric shaped catalyst bodies obtainable by the process according to the invention (the catalytically active composition obtainable in accordance with the invention; the catalyst obtainable in accordance with the invention), especially when it has been obtained in a not particularly homogeneous geometry, to be converted to a finely divided form (for example comminuted to powder or spall) for catalysis of a, for example, heterogeneously catalyzed partial oxidation of acrolein to acrylic acid (for example also in a fluidized or moving bed).

Particularly advantageously in accordance with the invention, the catalytically active composition obtainable in accordance with the invention will, however, be converted to a finely divided form (for example comminuted to powder or spall (for example by grinding)), and this finely divided form will be applied as a shell of the catalytically active composition to the outer surface of a geometric shaped support body (to obtain what is called an eggshell catalyst).

Typically, the application is effected with the aid of a liquid binder. It functions as an adhesion fluid, with the aid of which the finely divided catalytically active composition is fixed to the outer surface of the geometric shaped support body. Subsequently, the adhesion fluid is at least partly removed again from the coated geometric shaped support body (for example by passing over hot gas, as described in WO 2006/094766 A1).

Useful materials for the geometric shaped support bodies include, in accordance with the invention, especially aluminas, silicas, silicates such as clay, kaolin, steatite (preferably C-220 steatite from CeramTec (DE), or preferably with a low water-soluble alkali metal content), pumice, aluminum silicate, magnesium silicate, silicon carbide and zirconia. Appropriately in application terms, the geometric shaped support bodies are substantially inert with respect to the relevant partial oxidation (i.e., when they are used alone as "catalysts" for the corresponding heterogeneously catalyzed partial gas phase oxidation of, for example, acrolein to acrylic acid, they are largely inert, meaning that they cause essentially no conversion of the acrolein).

The outer surface of the geometric shaped support body may be either smooth or rough. Advantageously, the outer surface of the geometric shaped support body is rough, since increased surface roughness generally causes increased adhesion strength of the oxidic active composition shell applied.

Useful geometric shaped support bodies having distinct surface roughness include especially shaped support bodies having a grit layer on their outer surface (geometric shaped support bodies preferred in accordance with the invention are hollow cylinders with a grit layer on their outer surface).

The surface roughness $R_z$ of the outer surface of the geometric shaped support bodies is preferably in the range from 30 to 100 μm, more preferably in the range from 50 to 70 μm (determined to DIN 4768 Sheet 1 with a "Hommel Tester for DIN-ISO surface measurement parameters" from Hommelwerke). Particular preference is given to rough-surface geometric shaped support bodies from CeramTec made of C220 steatite.

The support materials may be porous or nonporous. The support material is preferably nonporous (the total volume of the pores of the geometric shaped support body is, based on the volume of the respective geometric shaped support bodies, advantageously ≤1% by volume). The specific (based on the unit of its mass) BET surface area of the support material is accordingly preferably low.

The geometric shaped support bodies may be of regular or irregular shape, preference being given in accordance with the invention to regularly shaped geometric shaped support bodies.

The longest dimension of the geometric shaped support bodies is normally in the range from 1 to 10 mm (the longest dimension is the longest direct line connecting two points on the outer surface of a shaped support body).

Preferably in accordance with the invention, spheres or (solid) cylinders, especially hollow cylinders (rings), are employed as geometric shaped support bodies. Favorable diameters for support spheres are 1 to 4 mm. If cylinders are used as geometric shaped support bodies, the length thereof is preferably 2 to 10 mm and the external diameter preferably 4 to 10 mm. In the case of rings, the wall thickness is additionally typically from 1 to 4 mm. Hollow cylindrical geometric shaped support bodies of length 3 to 6 mm, external diameter 4 to 8 mm and wall thickness 1 to 2 mm are geometric shaped support bodies very particularly preferred in accordance with the invention. Examples of ring geometries favorable in accordance with the invention for shaped support bodies include hollow cylinders of geometry 7 mm×3 mm×4 mm (external diameter×length×internal diameter) and of geometry 5 mm×3 mm×2 mm (external diameter×length×internal diameter). Geometric shaped support bodies favorable in accordance with the invention are also all shaped support bodies disclosed in Research Disclosure Database Number 532036 in August 2008 (especially all those disclosed by way of example). The production of eggshell catalysts CE and IE disclosed in the present document can also be performed with any annular shaped support body disclosed by way of example therein (especially with those of geometry 7 mm (external diameter)×4 mm (internal diameter)×3 mm (length or height)).

The thickness of the shell of catalytically active oxide composition applied to the outer surface of the geometric shaped support bodies (especially of the above-detailed annular shaped support bodies (the outer surface of which also includes the surface enclosing the cavity of the ring)) is, appropriately in application terms, generally 10 to 1000 μm. This shell thickness in eggshell catalysts obtainable in accordance with the invention is preferably 10 to 500 μm, more preferably 100 to 500 μm and most preferably 200 to 300 μm.

Advantageously, the shell thickness is very substantially homogeneous over an individual eggshell catalyst. In the case of production of a relatively large production batch of eggshell catalysts obtainable in accordance with the invention, the shell thickness is likewise very substantially homogeneous over several individual eggshell catalyst ring bodies. Appropriately in application terms, the aforementioned homogeneity of the shell thickness is frequently within the range of those figures which have been given in the working examples of DE 10360058 A1.

The finely divided catalytically active composition can be applied to the outer surface of the geometric shaped support body, for example, by first moistening the outer surface with the liquid binder in a controlled manner (for example by spraying). By contacting the geometric shaped support body thus moistened with the finely divided catalytically active oxidic composition obtained in accordance with the invention, a layer of the active composition is subsequently fixed on the moistened surface (for example, dust the moistened geometric shaped support bodies as described in EP 714700 A2 with the finely divided catalytically active composition (with the active composition powder)).

In this context, "moisten in a controlled manner" means that the support surface is appropriately moistened in such a way that it does have adsorbed liquid binder, but no liquid phase as such is visually apparent on the support surface.

If the support surface is too moist, the finely divided catalytically active multimetal oxide composition agglomerates to give separate agglomerates, rather than adhering to the surface. Details of this can be found in DE 2909671 A1 and in DE 10051419 A1, and also in EP 714700 A2. It will be appreciated that the operation can be repeated periodically to achieve an increased layer thickness. In this case, the coated base body becomes the new "support body", etc.

However, it is also possible to employ all other application processes acknowledged as prior art in EP 714700 A2 for production of the above-detailed eggshell catalysts.

Examples of useful liquid binders include water, an organic solvent or a solution of an organic substance (for example of an organic solvent) in water, or in an organic solvent, or in an aqueous solution of an organic solvent. Examples of organic binders include mono- or polyhydric organic alcohols, for example ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, and mono- or polyfunctional organic amides, for example formamide. Suitable organic binder promoter constituents (binder promoters) soluble in water, in an organic liquid or in a mixture of water and an organic liquid are, for example, monosaccharides and oligosaccharides such as glucose, fructose, sucrose and/or lactose.

Particularly advantageously, the liquid binder used is a solution consisting of 20 to 90% by weight of water and 10 to 80% by weight of an organic compound. The organic component in the aforementioned liquid binders is preferably 10 to 50% by weight and more preferably 20 to 30% by weight. Very particularly preferred liquid binders are solutions which consist of 20 to 90% by weight of water and 10 to 80% by weight of glycerol. Advantageously, the glycerol content in these aqueous solutions is 10 to 50% by weight and more preferably 20 to 30% by weight. One reason for the advantage of binders preferred in accordance with the invention is that they are able to fully satisfactorily wet both the finely divided catalytically active composition (or the finely divided precursor composition (see below)) and the outer surface of the geometric shaped support bodies.

The fineness of the finely divided catalytically active (oxidic) composition (or the precursor composition thereof (see below)) to be applied on the outer surface of the geometric shaped support body will of course be matched to the desired shell thickness. For the shell thickness range from 100 to 500 μm, suitable active composition powders are, for example, those of which at least 50% of the total number of the preferably granular powder particles pass through a sieve of mesh size (circular meshes) 1 to 20 μm or alternatively 1 to 10 μm, and wherein the numerical proportion of particles having a longest dimension above 50 μm (of particles which do not pass through a sieve of mesh size (circular meshes) 50 μm) is less than 10%. For the rest, the statements made on page 18 of WO 2005/120702 A1 apply correspondingly.

Preferably in accordance with the invention, inventive eggshell catalysts obtainable as described will be obtained by the mode of production described and detailed by way of example in EP 714700 A2 (see also WO 2011/134932 A1 and the working examples of DE 10360057 A1). An aqueous solution of 75% by weight of water and 25% by weight of glycerol is the preferred liquid binder. The process according to the invention for thermal treatment of the geometric shaped precursor bodies will, advantageously in accordance with the invention, be performed according to the procedure described and detailed by way of example in DE 10360057 A1.

The inventive procedure also comprises those processes for producing a catalytically active composition in which the shaping of geometric shaped (precursor) bodies with the (finely divided) mixture consisting of a spray powder P, at least one pulverulent oxide S of molybdenum and optionally one or more shaping assistants is effected in such a way that (in a manner corresponding to that described for the application of an active composition shell) a shell of this (finely divided) mixture (of the finely divided precursor composition) is applied directly as such a shell to the outer surface of a geometric shaped support body. In the course of the inventive thermal treatment of the geometric shaped (precursor) bodies thus obtained (which also comprises the at least partial removal of the liquid binder used for the application), inventive eggshell catalysts in which a shell of catalytically active composition has been applied on the outer surface of a (catalytically essentially inert) geometric shaped support body are obtained directly.

As already mentioned, catalytically active compositions obtainable in accordance with the invention are especially suitable for catalysis of a heterogeneously catalyzed partial gas phase oxidation of acrolein to acrylic acid (for example one as described in documents WO 2007/082827 A1, WO 2004/085365 A2, WO 2004/085367 A1, WO 2004/085368 A2, WO 2004/085369 A1, WO 2004/085370 A1, WO 2005/016861 A1, WO 2005/047226 A1 and WO 2005/042459 A1). They are notable especially in that a catalyst bed charged therewith, in the course of performance of the partial oxidation, has a long service life during which the target product is formed at high activity with high selectivity. The preferred use form of a catalytically active composition obtainable in accordance with the invention is that of an eggshell catalyst which preferably has an annular ring geometry (more preferably, the eggshell catalyst detailed by way of example in the example of the present document is used (for example in all working examples and in all comparative examples of the above WO documents (WO 2007/082827 A1, WO 2004/085365 A2, WO 2004/085367 A1, WO 2004/085368 A2, WO 2004/085369 A1, WO 2004/085370 A1, WO 2005/016861 A1, WO 2005/047226 A1 and WO 2005/042459 A1), in each of which it is capable of replacing the catalyst used therein; the statements made therein for the eggshell catalyst from the example of the present document also apply to the eggshell catalyst from the comparative example of the present document)).

In principle, catalytically active compositions obtainable in accordance with the invention are also suitable in a correspondingly advantageous manner for catalysis of the heterogeneously catalyzed partial gas phase oxidation of methacrolein to methacrylic acid.

The above is particularly true when the heterogeneously catalyzed partial gas phase oxidation of acrolein or methacrolein (i.e., in abbreviated form, of "(meth)acrolein") to acrylic acid or methacrylic acid (i.e., in abbreviated form, to "(meth)acrylic acid") is performed at high (meth)acrolein loads, as described, for example, in DE 10307983 A1, DE 19948523 A1, DE 19910508 A1, WO 2008/104577 A1, WO 2011/134932 A1, DE 19927624 A1 and DE 10360057 A1.

The heterogeneously catalyzed partial gas phase oxidation can be performed in a manner known per se. In other words, a reaction gas mixture comprising the (meth)acrolein, molecular oxygen and at least one inert diluent gas is conducted at elevated temperature through a catalyst bed, the catalysts of which comprise, as the active composition, at least one catalytically active composition obtainable in accordance with the invention, and the conversion thereof to (meth) acrylic acid is effected during the residence time of the (meth) acrolein in the catalyst bed. Preferably in accordance with the invention, the catalyst bed is a fixed catalyst bed. In principle, however, a fluidized bed or a moving bed is also useful for the process according to the invention. In general, steam as a constituent of the reaction gas mixture leads to an improvement in selectivity and activity. In addition, inert diluent gases having elevated molar specific heat, for example n-propane or $CO_2$, are advantageous. These are gases which, in the course of passage of the reaction gas mixture through the catalyst bed, are altered chemically to an extent of $\leq 5$ mol %, preferably to an extent of $\leq 3$ mol % and more preferably to an extent of $\leq 1$ mol % or not at all.

For performance of the gas phase partial oxidation of (meth)acrolein, heat exchanger reactors in particular are suitable. A heat exchanger reactor has at least one primary space and at least one secondary space, which are separated from one another by a dividing wall. In the at least one primary space is positioned the catalyst charge which comprises at least one catalytically active composition which is obtainable in accordance with the invention and through which a reaction gas mixture comprising (meth)acrolein flows. At the same time, a fluid heat carrier flows through the secondary space and heat exchange takes place between the two spaces through the dividing wall, the purpose of which is to monitor and to control the temperature of the reaction gas mixture on its way through the catalyst bed.

In general, the gas phase partial oxidation of the (meth) acrolein is performed in a shell-and-tube (heat exchanger) reactor having one or more temperature zones, as described, for example, in EP 700174 A1, EP 700893 A1, DE 19910508 A1, DE 19948523 A1, DE 19910506 A1, DE 19948241 A1, DE 2830765 A1, DE 2513405 A1, U.S. Pat. No. 3,147,084 A, DE 2201428 A1, EP 383224 A2, JP 2007-260588 A and JP 58096041A.

A fixed catalyst bed is present in the form of a corresponding bed of shaped catalyst bodies (optionally in a mixture with diluting inert geometric shaped bodies) in the metal tubes (catalyst tubes) of the shell-and-tube reactor, the temperature medium is, or the temperature media are, conducted around the metal tubes (in the case of more than one temperature zone, a corresponding number of spatially essentially separate temperature media are conducted around the metal tubes). The temperature medium is generally a salt melt. The reaction gas mixture is conducted through the catalyst tubes.

Alternatively, the fixed catalyst bed may, for example, also be within the spaces between thermoplates, through which a heat carrier flows, in a thermoplate reactor, as recommended, for example, in DE 10 2004 017 150 A1, DE 19952964 A1 and DE 10361456 A1.

The fixed catalyst bed may, as already stated, quite generally consist only of catalysts obtainable in accordance with the invention, but also of such catalysts diluted with inert geometric shaped bodies. The inert geometric shaped bodies may, for example, be the geometric shaped support bodies (support bodies) used for production of inventive eggshell catalysts. Upstream of and/or beyond the fixed bed catalyst may be disposed a bed purely of inert shaped bodies (such beds purely of inert shaped bodies are not normally included in the calculation of the space velocity of reaction gas or of a reaction gas component on the fixed catalyst bed).

Catalyst tubes used in a shell-and-tube reactor are customarily manufactured from ferritic steel and typically have a wall thickness of 1 to 3 mm. Their internal diameter is generally 20 to 30 mm, frequently 21 to 29 mm or 21 to 26 mm. Their length is appropriately 2 to 4 m.

Appropriately in application terms, the number of catalyst tubes accommodated in the shell-and-tube reactor runs to at least 5000, preferably to at least 10 000. Frequently, the number of catalyst tubes accommodated in the reactor vessel is 15 000 to 40 000. Shell-and-tube reactors having a number of catalyst tubes exceeding 50 000 are usually exceptional. Within the vessel, the catalyst tubes are normally arranged in homogeneous distribution (preferably 6 equidistant neighboring tubes per catalyst tube), the distribution appropriately being selected such that the separation of the central internal axes of mutually adjacent catalyst tubes (called the catalyst tube pitch) is 35 to 45 mm (cf., for example, EP-B 468290 A1).

A particularly favorable heat exchange medium for shell-and-tube reactors is the use of melts of salts such as potassium nitrate, potassium nitrite, sodium nitrite and/or sodium nitrate, or of low-melting metals such as sodium, mercury and alloys of different metals.

Charging of catalyst tubes in shell-and-tube reactors with catalysts obtainable in accordance with the invention (especially those detailed in the example (but also in the comparative example) of the present document) is advantageous particularly when the shell-and-tube reactor is operated at a (meth)acrolein space velocity on the catalyst charge of >130 l (STP)/l·h, or ≥150 l (STP)/l·h, or ≥160 l (STP)/l·h, or ≥170 l (STP)/l·h, or ≥180 l (STP)/l·h, or ≥200 l (STP)/l·h, or ≥220 l (STP)/l·h, or ≤240 l (STP)/l·h, or ≥260 l (STP)/l·h. Of course, such a catalyst charge is also advantageous in the case of smaller (e.g. ≤130 l (STP)/l·h, or ≤100 l (STP)/l·h, or ≤80 l (STP)/l·h, or ≤60 l (STP)/l·h) (meth)acrolein space velocities.

In general, the (meth)acrolein space velocity on the catalyst charge will be ≤400 l (STP)/l·h, or ≤350 l (STP)/l·h, or ≤300 l (STP)/l·h, or ≤280 l (STP)/l·h (corresponding space velocities can also be implemented in thermoplate reactors).

The space velocity of reaction gas input mixture on a fixed catalyst bed is understood in this document to mean the amount of reaction gas input mixture in standard liters (=l (STP); the volume in liters that the corresponding amount of reaction gas input mixture would occupy under standard conditions, i.e. at 0° C. and 1 atm (1.01 bar)) which is supplied to the fixed catalyst bed, based on the volume of the bed thereof (bed sections composed purely of inert material are not included in the volume of the bed; incidentally, the volume of a bed is the volume of the empty space occupied by the bed (or by the relevant sections thereof)), i.e. based on the bed volume thereof, per hour (->unit=l (STP)/l·h).

The space velocity may also be based only on one constituent of the reaction gas input mixture (for example only on the organic starting compound to be partially oxidized). In that case, it is correspondingly the volume of this constituent (for example of the organic starting compound of the partial oxidation) in standard liters which is supplied to the fixed catalyst bed, based on the volume of the bed thereof (bed sections composed purely of inert material are not included in the volume of the bed; incidentally, the volume of a bed is the volume of the empty space occupied by the bed (or by the relevant sections thereof)), per hour (->unit=l (STP)/l·h).

The volume-specific activity of the fixed catalyst bed will generally be configured such that it increases in flow direction of the reaction gas.

This can be achieved in a simple manner, for example, by decreasing the level of dilution of the fixed catalyst bed with inert shaped bodies in flow direction of the reaction gas.

Otherwise, the heterogeneously catalyzed partial oxidation with, for example, eggshell catalysts obtainable in accordance with the invention can quite generally be performed in all aspects as detailed, for example, by DE-A 10350822 A1. The (meth)acrolein content in the reaction gas input mixture may, for example, be at values of 3 or 6 to 15% by volume, frequently 4 or 6 to 10% by volume, or 5 to 8% by volume (based in each case on the total volume of the reaction gas input mixture).

The molar ratio of $O_2$:(meth)acrolein in the reaction gas input mixture will normally be ≥1. Typically, this ratio will be at values of ≤3. In many cases, the heterogeneously catalyzed (meth)acrolein partial oxidation to (meth)acrylic acid will be executed with a (meth)acrolein:oxygen:steam:inert gas volume ratio (l (STP)) present in the reaction gas input mixture of 1:(1 to 3):(0 to 20):(3 to 30), preferably of 1:(1 to 3):(0.5 to 10):(7 to 10).

Useful inert diluent gases (these are gases or mixtures of those gases which, in single pass of the reaction gas mixture through the catalyst bed (e.g. a fixed catalyst bed), are preserved chemically unchanged to an extent of at least 95 mol %, preferably to an extent of at least 97 mol % or to an extent of at least 99 mol %, and at best to an extent of 100 mol %) include $N_2$, $CO_2$, CO, noble gases, propane, ethane, methane, butane and/or pentane (i.e. each as a sole diluent gas or in a mixture with one other inert diluent gas or with a plurality of other inert diluent gases among these). The reaction temperatures of such a heterogeneously catalyzed (meth)acrolein partial oxidation are typically in the range from 200 to 400° C., generally from 220 to 380° C., in many cases from 230 to 350° C., frequently from 245 to 285° C. or from 245 to 265° C. The working pressure (absolute pressure) is normally 101.3 to 350 kPa, or 101.3 to 250 kPa, or 101.3 to 205 kPa (especially as the input pressure into the fixed catalyst bed). The (meth)acrolein partial oxidation with the catalysts obtainable in accordance with the invention can of course also be performed at working pressures below atmospheric pressure.

The (meth)acrolein conversion, based on a single pass of the reaction gas mixture through the, for example, fixed catalyst bed, is typically ≥90 mol %, frequently ≥98 mol %, and in many cases ≥99 mol %, or even ≥99.9 mol %.

Otherwise, the inventive partial oxidation process can be executed in a manner entirely corresponding to the teachings of DE 10 2007 019 597 A1 or of WO 2008/104577 A1, or of WO 2011/134932 A1.

More particularly, the source used for the (meth)acrolein required for the inventive partial oxidation may directly be the (meth)acrolein-comprising product gas mixture of a heterogeneously catalyzed partial oxidation of a $C_3/C_4$ precursor compound (e.g. propene or isobutene) of (meth)acrolein to (meth)acrolein, without any need to remove the (meth)acrolein from such a product gas mixture beforehand.

The selectivity S of (meth)acrylic acid formation (mol %) is understood in this document to mean:

$$S = \frac{\text{number of moles of (meth)acrolein converted to (meth)acrylic acid} \times 100 \text{ mol \%}}{\text{number of moles of (meth)acrolein converted overall}}$$

(the conversion numbers are each based on a single pass of the reaction gas mixture through the catalyst bed). A comparison of selectivities S of target product formation is appropriately based on equal reactant conversions.

An active composition (catalyst) leading to the same conversion at lower temperature under otherwise unchanged reaction conditions has a higher activity.

The conversion C of (meth)acrolein (mol %) is defined in a corresponding manner as:

$$C = \frac{\text{number of moles of (meth)acrolein converted}}{\text{number of moles of (meth)acrolein used}} \times 100 \text{ mol \%}$$

The (meth)acrylic acid can be removed from the product gas mixture of the partial oxidation in a known manner, for example by first converting the (meth)acrylic acid to the condensed phase by absorptive and/or condensative measures. Subsequent thermal separation processes, for example rectification and/or crystallization, can subsequently isolate (meth)acrylic acid in any purity from the condensed phase (cf., for example, DE 602004924 T2 and WO 2006/114428 A1 and the prior art cited in these documents).

Thus, the present application comprises especially the following embodiments of the invention:

1. A process for producing a catalytically active composition being a mixture of a multielement oxide comprising the elements Mo and V and at least one oxide of molybdenum, which comprises the process measures of
   using sources of the elemental constituents of the multielement oxide to obtain an aqueous solution, or an aqueous suspension with the proviso that each of the sources passes through the state of an aqueous solution in the course of obtaining the aqueous suspension,
   spray drying the aqueous solution or aqueous suspension to obtain a spray powder P,
   using the spray powder P with addition of at least one pulverulent oxide S of molybdenum and optionally with addition of one or more shaping assistants and after homogeneous mixing of said constituents to form geometric shaped precursor bodies using the resulting mixture, and
   thermally treating the geometric shaped precursor bodies to form the catalytically active composition.
2. The process according to embodiment 1, wherein the at least one pulverulent oxide S of molybdenum is at least one molybdenum oxide from the group consisting of $MoO_2$, $MoO_3$, $Mo_{18}O_{52}$, $Mo_8O_{23}$ and $Mo_4O_{11}$.
3. The process according to embodiment 2, wherein the at least one pulverulent oxide S of molybdenum is at least one molybdenum trioxide.
4. The process according to any of embodiments 1 to 3, wherein the specific BET surface area $SA_M$ of the at least one pulverulent oxide S of molybdenum is $\leq 20$ $m^2/g$.
5. The process according to any of embodiments 1 to 4, wherein the specific BET surface area $SA_M$ of the at least one pulverulent oxide S of molybdenum is $\leq 15$ $m^2/g$.
6. The process according to any of embodiments 1 to 5, wherein the specific BET surface area $SA_M$ of the at least one pulverulent oxide S of molybdenum is $\geq 10$ $m^2/g$.
7. The process according to any of embodiments 1 to 6, wherein the specific BET surface area $SA_M$ of the at least one pulverulent oxide S of molybdenum is $\geq 0.01$ $m^2/g$.
8. The process according to any of embodiments 1 to 7, wherein the specific BET surface area $SA_M$ of the at least one pulverulent oxide S of molybdenum is $\geq 0.05$ $m^2/g$.
9. The process according to any of embodiments 1 to 8, wherein the specific BET surface area $SA_M$ of the at least one pulverulent oxide S of molybdenum is $\geq 0.1$ $m^2/g$.
10. The process according to any of embodiments 1 to 9, wherein the specific BET surface area $SA_M$ of the at least one pulverulent oxide S of molybdenum is $\geq 0.5$ $m^2/g$.
11. The process according to any of embodiments 1 to 10, wherein the specific BET surface area $SA_M$ of the at least one pulverulent oxide S of molybdenum is $\geq 1$ $m^2/g$.
12. The process according to any of embodiments 1 to 11, wherein the particle diameter $d_{90}$ of the at least one pulverulent oxide S of molybdenum is $\leq 20$ µm.
13. The process according to any of embodiments 1 to 12, wherein the particle diameter $d_{90}$ of the at least one pulverulent oxide S of molybdenum is $\leq 10$ µm.
14. The process according to any of embodiments 1 to 13, wherein the particle diameter $d_{90}$ of the at least one pulverulent oxide S of molybdenum is $\leq 5$ µm.
15. The process according to any of embodiments 1 to 14, wherein the particle diameter $d_{90}$ of the at least one pulverulent oxide S of molybdenum is $\leq 3$ µm.
16. The process according to any of embodiments 1 to 15, wherein the particle diameter $d_{90}$ of the at least one pulverulent oxide S of molybdenum is $\leq 2$ µm.
17. The process according to any of embodiments 1 to 16, wherein the particle diameter $d_{10}$ of the at least one pulverulent oxide S of molybdenum is $\geq 50$ nm.
18. The process according to any of embodiments 1 to 17, wherein the particle diameter $d_{10}$ of the at least one pulverulent oxide S of molybdenum is $\geq 75$ nm.
19. The process according to any of embodiments 1 to 18, wherein the particle diameter $d_{10}$ of the at least one pulverulent oxide S of molybdenum is $\geq 100$ nm.
20. The process according to any of embodiments 1 to 19, wherein the particle diameter $d_{10}$ of the at least one pulverulent oxide S of molybdenum is $\geq 150$ nm or $\geq 200$ nm.
21. The process according to any of embodiments 1 to 20, wherein the particle diameter $d_{10}$ of the spray powder P is $\geq 1$ µm and the particle diameter $d_{90}$ of the spray powder P is $\leq 70$ µm.
22. The process according to any of embodiments 1 to 21, wherein the at least one pulverulent oxide S of molybdenum, based on the weight of the catalytically active composition produced in the process, is added in an amount of $>0$ and $\leq 50\%$ by weight.
23. The process according to any of embodiments 1 to 22, wherein the at least one pulverulent oxide S of molybdenum, based on the weight of the catalytically active composition produced in the process, is added in an amount of $>0$ and $\leq 45\%$ by weight.
24. The process according to any of embodiments 1 to 23, wherein the at least one pulverulent oxide S of molybdenum, based on the weight of the catalytically active composition produced in the process, is added in an amount of $>0$ and $\leq 40\%$ by weight.
25. The process according to any of embodiments 1 to 24, wherein the at least one pulverulent oxide S of molybdenum, based on the weight of the catalytically active composition produced in the process, is added in an amount of $\geq 1$ and $\leq 35\%$ by weight.
26. The process according to any of embodiments 1 to 25, wherein the at least one pulverulent oxide S of molybdenum, based on the weight of the catalytically active composition produced in the process, is added in an amount of $\geq 3$ and $\leq 30\%$ by weight.
27. The process according to any of embodiments 1 to 26, wherein the at least one pulverulent oxide S of molybdenum, based on the weight of the catalytically active composition produced in the process, is added in an amount of $\geq 5$ and $\leq 30\%$ by weight.
28. The process according to any of embodiments 1 to 27, wherein the at least one pulverulent oxide S of molybdenum, based on the weight of the catalytically active composition produced in the process, is added in an amount of ≥10 and ≤25% by weight.
29. The process according to any of embodiments 1 to 28, wherein the at least one pulverulent oxide S of molybdenum, based on the weight of the catalytically active composition produced in the process, is added in an amount of ≥10 and ≤20% by weight.
30. The process according to any of embodiments 1 to 29, wherein the at least one pulverulent oxide S of molybdenum, based on the weight of the catalytically active composition produced in the process, is added in an amount of ≥10 and ≤15% by weight.
31. The process according to any of embodiments 1 to 30, wherein the molar proportion of the element Mo in the total amount of the elements other than oxygen in the multielement oxide comprising the elements Mo and V is 5 to 95 mol %.
32. The process according to any of embodiments 1 to 31, wherein the molar proportion of the element Mo in the total amount of the elements other than oxygen in the multielement oxide comprising the elements Mo and V is 10 to 90 mol %.
33. The process according to any of embodiments 1 to 32, wherein the molar proportion of the element Mo in the total amount of the elements other than oxygen in the multielement oxide comprising the elements Mo and V is 15 to 85 mol %.
34. The process according to any of embodiments 1 to 33, wherein the molar proportion of the element Mo in the total amount of the elements other than oxygen in the multielement oxide comprising the elements Mo and V is 20 to 80 mol %.
35. The process according to any of embodiments 1 to 34, wherein the molar Mo/V ratio of the molar amounts of Mo and V present in the multielement oxide is 15:1 to 1:1.
36. The process according to any of embodiments 1 to 35, wherein the molar Mo/V ratio of the molar amounts of Mo and V present in the multielement oxide is 12:1 to 2:1.
37. The process according to any of embodiments 1 to 36, wherein the multielement oxide, as well as Mo, V and O, also comprises at least one of the elements Nb and W.
38. The process according to embodiment 37, wherein the molar Mo/(W+Nb) ratio of the molar amount of Mo present in the multielement oxide to the total molar amount of (W+Nb) present in the multielement oxide is 80:1 to 1:4.
39. The process according to any of embodiments 1 to 38, wherein the multielement oxide additionally comprises Cu.
40. The process according to embodiment 39, wherein the molar Mo/Cu ratio of the molar amounts of Mo and Cu present in the multielement oxide is 30:1 to 1:3.
41. The process according to any of embodiments 37 to 40, wherein the multielement oxide additionally comprises at least one of the elements Ta, Cr, Ce, Ni, Co, Fe, Mn, Zn, Sb, Bi, alkali metals (Li, Na, K, Rb, Cs), H, alkaline earth metals (Mg, Ca, Sr, Ba), Si, Al, Ti and Zr.
42. The process according to any of embodiments 1 to 30, wherein the stoichiometry of the multielement oxide satisfies the following general stoichiometry I:

    (I)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40, and
n=a number which is determined by the valency and frequency of the elements in I other than oxygen.
43. The process according to embodiment 42, wherein the variables of the general stoichiometry I are defined as follows:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=2.5 to 5,
b=0.5 to 2,
c=0.5 to 3,
d=0 to 2,
e=0 to 0.2,
f=0 to 1,
g=0 to 15, and
n=a number which is determined by the valency and frequency of the elements in I other than oxygen.
44. The process according to any of embodiments 1 to 30, wherein the stoichiometry of the multielement oxide satisfies the following general stoichiometry II:

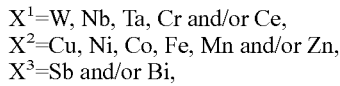    (II)

in which the variables are each defined as follows:
$X^1$=W and/or Nb,
$X^2$=Cu and/or Ni,
$X^5$=Co and/or Sr,
$X^6$=Si and/or Al,
a=3 to 4.5,
b=1 to 1.5,
c=0.75 to 2.5,
f=0 to 0.5,
g=0 to 8, and
n=a number which is determined by the valency and frequency of the elements in II other than oxygen.
45. The process according to any of embodiments 1 to 30, wherein the multielement oxide comprises, as well as the elements Mo and V, at least one of the two elements Te and Sb, and at least one of the elements from the group consisting of Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In.
46. The process according to any of embodiments 1 to 30, wherein the multielement oxide comprises, as well as the elements Mo and V, at least one of the two elements Te and Sb, and at least one of the elements from the group consisting of Nb, Ta, W and Ti.
47. The process according to any of embodiments 1 to 30, wherein the multielement oxide comprises, as well as the elements Mo and V, at least one of the two elements Te and Sb, and the element Nb.
48. The process according to any of embodiments 1 to 30, wherein the stoichiometry of the multielement oxide satisfies the following general stoichiometry III:

    (III)

where

M¹=Te and/or Sb,

M²=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In, b=0.01 to 1, c=>0 to 1, and d=>0 to 1.

49. The process according to any of embodiments 1 to 48, wherein the sources of the elemental constituents of the multielement oxide comprise an oxide, halide, nitrate, formate, oxalate, acetate and/or carbonate of one or more elemental constituents and/or a hydrate thereof.

50. The process according to any of embodiments 1 to 49, wherein one source used for the elemental constituents of the multielement oxide is one or more than one oxo compound of the elemental constituents Mo, V, W and Nb.

51. The process according to embodiment 50, wherein one or more than one oxo compound is an ammonium oxometalate from the group consisting of ammonium metaniobate, ammonium metavanadate, ammonium molybdate, ammonium heptamolybdate tetrahydrate and ammonium paratungstate heptahydrate.

52. The process according to any of embodiments 1 to 51, wherein the aqueous solution or aqueous suspension from which the spray powder P is obtained comprises ammonia, nitric acid, hydrochloric acid, acetic acid, formic acid, oxalic acid, ammonium nitrate, ammonium chloride, ammonium carbonate, ammonium hydrogencarbonate, ammonium hydroxide, ammonium acetate, ammonium formate, ammonium oxalate, ethylenediaminetetraacetic acid, stearic acid, malonic acid, starch, cellulose, nutshells and/or finely ground polymer.

53. The process according to any of embodiments 1 to 52, wherein the shaping of the mixture comprising the spray powder P and the at least one pulverulent oxide S of molybdenum to the geometric shaped precursor bodies is effected by press agglomeration of the mixture.

54. The process according to embodiment 53, wherein the mixture to be shaped to the geometric shaped precursor bodies comprises at least one shaping assistant from the group consisting of graphite, carbon black, polyethylene glycol, stearic acid, salts of stearic acid, starch, polyacrylic acid, mineral oil, vegetable oil, water, boron nitride, boron trifluoride, glycerol, fine Teflon powder and cellulose ether.

55. The process according to embodiment 53 or 54, wherein the mixture to be shaped to the geometric shaped precursor bodies comprises at least one shaping assistant from the group consisting of microfibers of glass, asbestos, silicon carbide and potassium titanate.

56. The process according to embodiment 54 or 55, wherein the mixture to be shaped to the geometric shaped precursor bodies, based on the total amount thereof, comprises 0.1 to 30% by weight of shaping assistants.

57. The process according to any of embodiments 54 to 56, wherein the mixture to be shaped to the geometric shaped precursor bodies, based on the total amount thereof, comprises 0.2 to 20% by weight of shaping assistants.

58. The process according to any of embodiments 54 to 57, wherein the mixture to be shaped to the geometric shaped precursor bodies, based on the total amount thereof, comprises 0.5 to 10% by weight of shaping assistants.

59. The process according to any of embodiments 1 to 52, wherein the shaping of the mixture comprising the spray powder P and the at least one pulverulent oxide S of molybdenum to the geometric shaped precursor bodies is effected by extrusion of the mixture.

60. The process according to embodiment 59, wherein the mixture to be shaped to the geometric shaped precursor bodies comprises at least one liquid as a shaping assistant.

61. The process according to embodiment 60, wherein the at least one liquid comprises one or more than one organic carboxylic acid having 2 to 4 carbon atoms, water, an aqueous solution, or the constituents of an aqueous solution.

62. The process according to embodiment 60 or 61, wherein the at least one liquid comprises at least one of the organic carboxylic acids formic acid, acetic acid, propionic acid, fumaric acid and maleic acid.

63. The process according to any of embodiments 60 to 62, wherein the at least one liquid comprises the carboxylic acid acetic acid.

64. The process according to any of embodiments 61 to 63, wherein the mixture to be shaped to the geometric shaped precursor bodies, based on the content of spray powder P therein, comprises a total amount of 5 to 10% by weight of organic carboxylic acid.

65. The process according to any of embodiments 60 to 64, wherein the mixture to be shaped to the geometric shaped precursor bodies, based on the weight thereof, comprises 5 to 40% by weight of water.

66. The process according to any of embodiments 60 to 65, wherein the mixture to be shaped to the geometric shaped precursor bodies, based on the weight thereof, comprises 10 to 30% by weight of water.

67. The process according to any of embodiments 1 to 66, wherein the geometric shaped precursor body is a sphere, a solid cylinder, a strand or a ring.

68. The process according to any of embodiments 1 to 67, wherein the geometric shaped precursor body has a longest dimension (longest direct line connecting two points on the outer surface thereof) of 2 to 10 mm.

69. The process according to any of embodiments 1 to 68, wherein the thermal treatment of the geometric shaped precursor bodies comprises a calcination at 200 to 600° C.

70. The process according to any of embodiments 1 to 69, wherein the thermal treatment of the geometric shaped precursor bodies comprises a calcination at 300 to 450° C.

71. The process according to any of embodiments 1 to 70, wherein the thermal treatment of the geometric shaped precursor bodies comprises a calcination at 300 to 400° C.

72. The process according to any of embodiments 1 to 71, wherein the thermal treatment of the geometric shaped precursor bodies is effected under an oxidative gas atmosphere.

73. The process according to any of embodiments 1 to 72, wherein the thermal treatment of the geometric shaped precursor bodies is effected under air.

74. The process according to any of embodiments 69 to 71, wherein the calcination is effected under a gas atmosphere comprising 0.5 to 10% by volume, or under one comprising 1 to 5% by volume, of molecular oxygen.

75. The process according to any of embodiments 69 to 74, wherein the calcination is effected under a gas atmosphere comprising $O_2$ and $NH_3$.

76. The process according to any of embodiments 69 to 75, wherein the calcination extends over a period of 0.5 h to 24 h.

77. The process according to any of embodiments 1 to 76, wherein the catalytically active composition is converted to a finely divided form and the finely divided form is applied as a shell of the catalytically active composition to the outer surface of a geometric shaped support body.
78. The process according to embodiment 77, wherein the geometric shaped support body consists of alumina, silica, clay, kaolin, steatite, pumice, aluminum silicate, magnesium silicate, silicon carbide and/or zirconia.
79. The process according to embodiment 77 or 78, wherein the surface roughness $R_z$ of the outer surface of the geometric shaped support body is in the range from 30 to 100 µm.
80. The process according to any of embodiments 77 to 79, wherein the surface roughness $R_z$ of the outer surface of the geometric shaped support body is in the range from 50 to 70 µm.
81. The process according to any of embodiments 77 to 80, wherein the total volume of the pores of the geometric shaped support body, based on the volume of the respective geometric shaped support body, is ≤1% by volume.
82. The process according to any of embodiments 77 to 81, wherein the geometry of the shaped support body is that of a sphere, cylinder or ring.
83. The process according to any of embodiments 77 to 82, wherein the geometry of the shaped support body is that of a sphere having an external diameter of 1 to 4 mm.
84. The process according to any of embodiments 77 to 82, wherein the geometry of the shaped support body is that of a cylinder having a length of 2 to 10 mm and an external diameter of 4 to 10 mm.
85. The process according to any of embodiments 77 to 82, wherein the geometry of the shaped support body is that of a ring having a length of 2 to 10 mm, an external diameter of 4 to 10 mm and a wall thickness of 1 to 4 mm.
86. The process according to any of embodiments 77 to 82, wherein the geometry of the shaped support body is that of a ring having a length of 3 to 6 mm, an external diameter of 4 to 8 mm and a wall thickness of 1 to 2 mm.
87. The process according to any of embodiments 77 to 86, wherein the thickness of the shell of catalytically active composition applied is 10 to 1000 µm.
88. The process according to any of embodiments 77 to 87, wherein the thickness of the shell of catalytically active composition applied is 10 to 500 µm.
89. The process according to any of embodiments 77 to 88, wherein the thickness of the shell of catalytically active composition applied is 100 to 500 µm.
90. The process according to any of embodiments 77 to 89, wherein the thickness of the shell of catalytically active composition applied is 300 to 500 µm.
91. The process according to any of embodiments 77 to 90, wherein the catalytically active composition is applied to the outer surface of the geometric shaped support body with the aid of a liquid binder.
92. The process according to embodiment 91, wherein the liquid binder is water, an organic solvent, a solution of an organic substance in water, a solution of an organic substance in an organic solvent and/or a solution of an organic substance in an aqueous solution of an organic solvent.
93. The process according to embodiment 91, wherein the liquid binder is a solution consisting of 20 to 90% by weight of water and 10 to 80% by weight of an organic compound.
94. The process according to embodiment 91, wherein the liquid binder consists of 20 to 90% by weight of water and 10 to 80% by weight of glycerol.
95. The process according to embodiment 94, wherein the proportion of glycerol in the liquid binder is 10 to 50% by weight or 20 to 30% by weight.
96. The process according to any of embodiments 91 to 95, wherein the application of the shell of finely divided catalytically active composition to the outer surface of a geometric shaped support body is followed by removal of at least a portion of the liquid binder used for the application.
97. The process according to any of embodiments 1 to 52, wherein the shaping of the mixture comprising the spray powder P and the at least one pulverulent oxide S of molybdenum to the geometric shaped precursor bodies is effected in such a way that a shell of this mixture is applied directly to the outer surface of a geometric shaped support body.
98. The process according to embodiment 96 or 97, wherein the shell of catalytically active composition has pores and that diameter of the pores which makes the greatest contribution to the total volume of the pores is 0.03 to 0.8 µm.
99. The process according to any of embodiments 1 to 98, wherein the specific BET surface area of the catalytically active composition is 5 to 40 m²/g.
100. The process according to any of embodiments 1 to 99, wherein the specific BET surface area of the catalytically active composition is 10 to 30 m²/g.
101. The process according to any of embodiments 1 to 100, wherein the specific BET surface area of the catalytically active composition is 10 to 20 m²/g.
102. A catalyst obtainable by a process according to any of embodiments 1 to 101.
103. A catalyst consisting of a geometric shaped support body and a catalytically active composition present on the outer surface of the geometric shaped support body, and optionally binder, wherein the catalytically active composition is obtainable by a process according to any of embodiments 1 to 76 or according to embodiment 97.
104. A catalyst consisting of a geometric shaped support body and a catalytically active composition applied to the outer surface of the geometric shaped support body, and optionally binder, wherein the catalytically active composition is obtainable by a process according to any of embodiments 1 to 76.
105. The catalyst according to either of embodiments 103 and 104, wherein the specific BET surface area of the catalytically active composition thereof is 5 to 40 m²/g.
106. The catalyst according to any of embodiments 103 to 105, wherein the specific BET surface area of the catalytically active composition thereof is 10 to 30 m²/g.
107. The catalyst according to any of embodiments 103 to 106, wherein the specific BET surface area of the catalytically active composition thereof is 10 to 20 m²/g.
108. The catalyst according to any of embodiments 103 to 107, wherein the shell of catalytically active composition has pores and that diameter of the pores which makes the greatest contribution to the total volume of the pores is 0.03 to 0.8 µm.
109. A process for heterogeneously catalyzed partial gas phase oxidation of (meth)acrolein to (meth)acrylic acid, wherein the catalyst used for the heterogeneously catalyzed partial gas phase oxidation is at least one catalyst according to any of embodiments 102 to 108.
110. The process according to embodiment 109, wherein the catalyst is part of a fixed catalyst bed with a (meth)acrolein space velocity of 50 l (STP)/l·h to 250 l (STP)/l·h.

EXAMPLE AND COMPARATIVE EXAMPLE

A) Production of an Annular Comparative Eggshell Catalyst CE

Figure 4A:
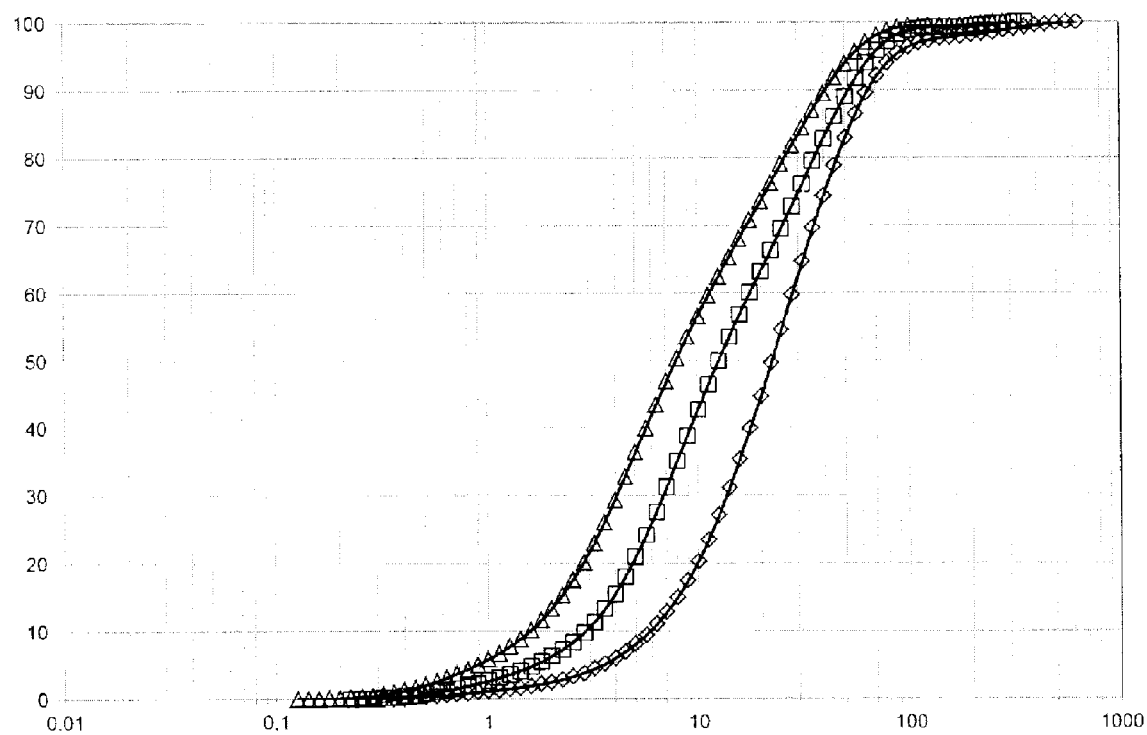
FIGS. 4a and 4b show size distributions of the particles of the spray powder obtained.
Figure 4B:
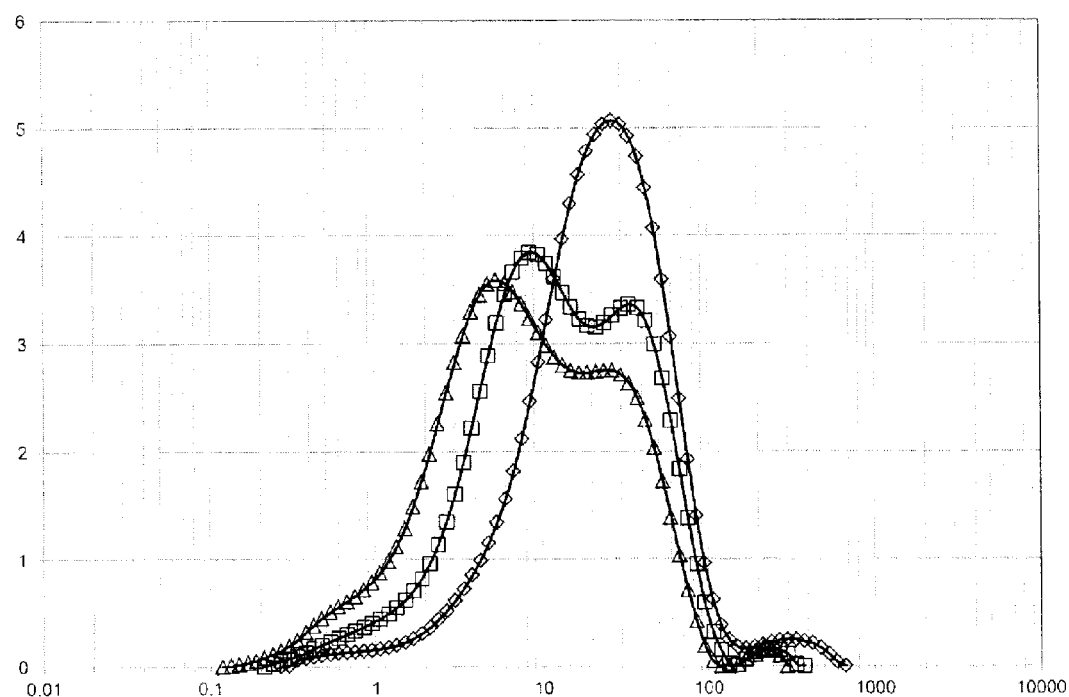

As described in working example 1A of WO 2011/134932 A1, a catalytically active multielement oxide composition of the stoichiometry $Mo_{12}V_3W_{1.2}Cu_{1.2}O_x$ was produced (cf. page 9 of WO 2011/134932; the size distribution of the particles of the spray powder obtained is shown in FIGS. 4a and 4b of this application (of the present document) as a function of the dispersion pressure of the compressed air used for dry dispersion (◇=1.1 bar abs.; □=2.0 bar abs.; Δ=4.5 bar abs.); the residual water content of the spray powder was 4.2% by weight based on the weight of the spray powder; the kneaded material was extruded as in B) of the present document and the extrudates were dried in an air circulation drying cabinet as in B) of the present document; the residual water content of the dried extrudates was (based on the weight thereof) 1.97% by weight; the calcination weight loss of the dried extrudates was (based on the weight thereof) 22.15% by weight (to measure the calcination weight loss, as always in the present document, a 15 g sample of the dried extrudates was introduced into a ceramic crucible which had been cooled to 25° C., having previously been calcined at 600° C. under air for 3 h; the ceramic crucible was then introduced in the presence of air into a muffle furnace (model: LE 14/11/P300, capacity=20 l) from Nabertherm Schweiz AG in CH-4614 Hägendorf; the muffle furnace was closed and the calcination material present was heated first from 25° C. to 500° C. in a linear manner within 1 h without further air supply; subsequently, the calcination material temperature of 500° C. was maintained for 3 h and then the muffle furnace and the calcination material present therein were left to cool in an essentially linear manner to 25° C. within 5 h; the difference in the sample weights before and after calcination, based on the sample weight before calcination, gives the calcination weight loss in % by weight).

The catalytically active multielement oxide composition removed from the rotary oven was subsequently ground to a finely divided powder in a Retsch ZM 200 mill (rotor type: 24-tooth rotor; sieve size (trapezoid holes): 0.12 mm; 18 000 revolutions per minute), of which 50% of the powder particles passed through a sieve of mesh size (circular meshes) 1 to 10 μm and wherein the numerical proportion of particles having a longest dimension above 50 μm (of particles which did not pass through a sieve of mesh size (circular meshes) 50 μm) was less than 1%.

The size distribution of the particles of the above ground catalytically active multielement oxide composition powder is shown in FIGS. 3*a* and 3*b* of this application (of this document) as a function of the dispersion pressure of the compressed air used for dry dispersion (◇=1.1 bar abs.; □=2.0 bar abs.; Δ=4.5 bar abs.). In FIG. 3*a*, the abscissa shows, in a logarithmic plot (on a logarithmic scale to base 10)), the particle diameter (the particle dimension) in μm, and the ordinate value on the distribution curve corresponding to a particular particle diameter on the abscissa shows the X % of the total particle volume which consists of particles having this particle dimension. In FIG. 3*b*, the abscissa, again in a logarithmic plot (on a logarithmic scale to base 10), shows the particle diameter (the particle dimension) in μm. The ordinate here, however, shows the proportion by volume of the total particle volume that has the particular diameter or a smaller diameter.

The analysis method which forms the basis of the particle diameter distribution of FIGS. 3*a* and 3*b* is laser diffraction, which has already been detailed in this document. This was done by conducting the multielement oxide composition powder through a dispersing channel into the Sympatec RODOS dry disperser (Sympatec GmbH, System-Partikel-Technik, Am Pulverhaus 1, D-38678 Clausthal-Zellerfeld), dry dispersing it there with compressed air (which had the respective dispersion pressure of 1.1 or 2 or 4.5 bar abs.) and blowing it into the measurement cell in a free jet. The Malvern Mastersizer S laser diffraction spectrometer (Malvern Instruments, Worcestershire WR14 1AT, United Kingdom) was then used to determine the volume-based particle diameter distribution therein to ISO 13320 (obscuration 3-7%).

1.74 kg of the ground $Mo_{12}V_3W_{1.2}Cu_{1.2}O_x$ powder, which had the particle size distributions shown in FIGS. 3*a* and 3*b* of this document as a function of the dispersion pressure employed, were admixed with 0.261 kg (=15% by weight based on the 1.74 kg of multielement oxide composition) of finely divided $MoO_3$ (this was "pure Molybdenum Oxide (POC)" from Climax Molybdenum Marketing Corporation, Phoenix (Ariz.), USA), which had been ground beforehand in a spiral mill (constructed in-house at BASF SE with a grinding space diameter of 450 mm) and, after grinding, had the particle diameter distributions according to FIGS. 2*a* and 2*b* of this document as a function of the dispersion pressure employed in each case (◇=1.1 bar abs.; □=2.0 bar abs.; Δ=4.5 bar abs.)).

Table 1 below shows the respective values for $d_{10}$, $d_{50}$ and $d_{90}$ (in μm) before and after grinding for the finely divided $MoO_3$ as a function of the dispersion pressure employed in each case.

TABLE 1

| $MoO_3$ | Dispersion pressure [bar abs.] | $d_{10}$ [μm] | $d_{50}$ [μm] | $d_{90}$ [μm] |
|---|---|---|---|---|
| before grinding | 1.1 | 87.7 | 233.95 | 440.18 |
| | 2.0 | 31.27 | 186.93 | 381.42 |
| | 4.5 | 0.71 | 90.13 | 292.86 |
| after grinding | 1.1 | 18.52 | 41.12 | 167.14 |
| | 2.0 | 0.39 | 0.78 | 1.89 |
| | 4.5 | 0.35 | 0.68 | 1.33 |

The specific BET surface area of the $MoO_3$ before grinding was 3±1 $m^2/g$.

The specific BET surface area of the $MoO_3$ after grinding was 5±1 $m^2/g$.

The $MoO_3$ was added in portions (five portions of equal size) within 5 minutes to the initial charge of ground $Mo_{12}V_3W_{1.2}Cu_{1.2}O_x$ powder in an Eirich RV 02 intensive mixer (from Gustav Eirich GmbH & Co. KG in D-74736 Hardheim). The agitator and pan of the Eirich mixer were switched off and back on again for each $MoO_3$ addition (settings: pan: level 1; agitator: level 2). After the $MoO_3$ powder had been added completely, the mixture present in the Eirich intensive mixer was additionally mixed homogeneously over a further period of 2 minutes.

The finely divided mixture thus obtained (its specific internal total pore surface area was 8.6 $m^2/g$; its specific internal total pore volume (the total intrusion volume) was 0.42 ml/g) was, as described in comparative example 1A of WO 2011/134932 A1 on page 8 ff., used to produce an annular comparative catalyst CE. The annular comparative eggshell catalysts CE removed from the air circulation drying cabinet (UM 400 from Memmert GmbH+Co. KG in DE 91126 Schwabach; capacity=53 l; air flow rate=800 l (STP)/h; the temperature in the air circulation drying cabinet (including the air temperature) was 300° C. during the drying operation; the drying material was on a perforated metal sheet positioned in the center of the drying cabinet during the drying (the hole diameter of the passage orifices distributed homogeneously over the perforated metal sheet=0.5 cm; the orifice ratio of the perforated metal sheet was 60%; the total cross-sectional area of the perforated metal sheet was 35 cm×26 cm=910 $cm^2$) in the form of a bed (layer height=2 cm)) had, based on the total mass thereof, an oxidic shell fraction of 22.7% by weight. The specific BET surface area of the comparative eggshell catalysts CE was 3.15 m²/g. The geometric shaped support bodies used were rings (external diameter 7 mm, length 3 mm and internal diameter 4 mm) of C220 steatite having a surface roughness $R_z$ of 45 μm (grit layer) from CeramTec. The total pore volume of the support body based on the volume of the shaped support body composition was ≤1% by volume. The specific BET surface area of the geometric shaped support bodies was 0.04 m²/g.

Thus, the specific BET surface area X of the active composition shell of the comparative eggshell catalysts CE is calculated from $$0.227 \text{ m}^2/\text{g} \times X \text{ m}^2/\text{g} + 0.773 \times 0.04 \text{ m}^2/\text{g} = 3.15 \text{ m}^2/\text{g}$$

to be X=13.7 m²/g.

Studies of the pore properties of the active composition shell of the comparative eggshell catalysts CE gave the following results:

The specific internal total pore surface area of the pores studied in the active composition shell of the comparative eggshell catalysts CE was 6.71 m²/g.

The corresponding specific total pore volume was 0.3 ml/g.

Figure 5:
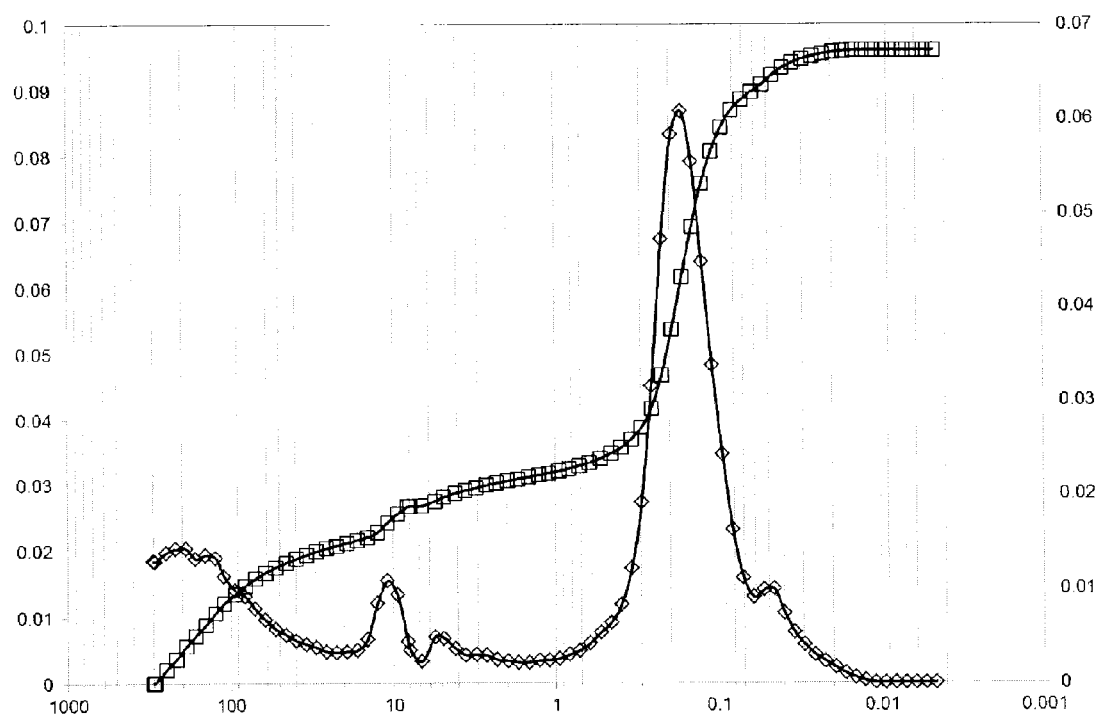
FIG. 5 shows a pore diameter distribution of the pores of the active composition shell of the comparative catalysts CE.

FIG. 5 of the present document shows the pore diameter distribution of the pores of the active composition shell of the comparative catalysts CE. On the abscissa is plotted the respective pore diameter in μm (logarithmic plot to base 10). On the left-hand ordinate is plotted the logarithm (to base 10) of the differential contribution in ([ml]/[g of eggshell catalyst]) of the respective pore diameter to the specific (based here on the overall composition formed from the composition of the geometric shaped support body and of the composition of the active composition shell) total pore volume (◇ curve). The maximum indicates the pore diameter having the greatest contribution to the (specific) total pore volume. On the right-hand ordinate is plotted, in ([ml]/[g of eggshell catalyst]), the integral over the individual contributions of each of the pore diameters to the aforementioned specific total pore volume (the cumulative contribution to the aforementioned specific total pore volume) (□ curve). The end point is the (specific) total pore volume based on the overall composition of geometric shaped support body and active composition (total intrusion volume). Division of this value by 0.227 results in the specific total pore volume based on the active composition.

Figures relating to the pore properties of solid substances always relate in the present document (unless explicitly stated otherwise) to an analysis of the respective solid by the method of mercury porosimetry. This method uses mercury, a liquid which does not wet most substances, to obtain information about the pore properties of the porous solid studied.

This involves immersing the previously outgassed (in order to outgas any liquid present in the porous structure) porous system (the sample to be studied) into a mercury bath, the pressure of which can be varied.

Since the mercury does not wet the sample material, the mercury need not be forced into the pores of the sample (establishment of equilibrium is awaited at the respective pressure). The penetration of the mercury into pores of relatively high cross-sectional area proceeds at comparatively lower pressures, whereas the penetration of the mercury into narrower pores requires a comparatively higher pressure. Assuming the presence of circular cylindrical pores, it is possible with the aid of the Washburn equation to determine the relationship of the external pressure required to force the liquid mercury to intrude into the pores of a certain diameter against the surface tension of the mercury (mercury intrusion) to said diameter. The pressure range employed in the course of the mercury porosimetry study correlates to the range of pore diameters covered.

The mercury intrusion curves determined experimentally at 25° C. can subsequently be used to extract, by calculation, over the range of pore diameters covered, the diameter distribution of the pores, the total internal surface area of the pores and the total internal volume of the pores (the total intrusion volume; the total pore volume) (cf. Inaugural Dissertation "Eigenschaften and Einsatzmöglichkeiten von Aerogelfenstern im Vergleich mit konventionellen sowie evakuierten Fenstern" [Properties and Possible Uses of Aerogel Windows compared to Conventional and Evacuated Windows] by Georges Reber (1991) at the Faculty of Philosophy and Natural Sciences of the University of Basle). The Micromeritics Auto Pore IV 9520 measuring instrument described hereinafter comprises standard calculation programs suitable for these purposes.

In this document, all figures relating to the pore properties of solid substances, unless explicitly stated otherwise, are based on determinations by the method of mercury porosimetry employing an Auto Pore IV 9520 instrument from Micromeritics in Norcross, Ga. 30093-1877, USA. In the case of examination of powders, the amount of sample introduced into the sample space in each case was 2.5 g. In the case of examination of eggshell catalysts, 5 pieces of the respective eggshell catalyst were each introduced into the sample space (the contribution of the pores of the geometric shaped support body of the eggshell catalyst was negligible in the cases examined compared to the contribution of the pores of the active composition shell).

The sample space was continued into an elongated capillary, such that slight pressure changes corresponded to distinct changes in the length of the mercury thread projecting into the capillary. The capillary volume utilized was in all cases between 25 and 91% by volume, based on the total capillary volume.

Before commencement of a particular sample analysis, the sample space (at 25° C.) was in each case evacuated down to an internal pressure of $9.3 \times 10^{-4}$ bar, and the sample was degassed at this temperature and at this pressure for 20 minutes. Thereafter, the mercury was forced into the sample space at pressures rising over the time up to a final pressure of 4137 bar. The starting pressure was 0.04 bar. This corresponds to a range of pore diameters covered of 0.003 μm to 360 μm.

B) Production of an Annular Inventive Eggshell Catalyst IE

As described for the production of the multielement oxide of the stoichiometry $Mo_{12}V_3W_{1.2}Cu_{1.2}O_n$ in working example 1A on page 9 of WO 2011/134932 A1, a corresponding spray powder was obtained. The size distribution of the particles of the spray powder is shown in FIGS. 4a and 4b of this application (of the present document) as a function of the dispersion pressure of the compressed air used for dry dispersion (◇=1.1 bar abs.; □=2.0 bar abs.; Δ=4.5 bar abs.).

In FIG. 4a, the abscissa shows, in a logarithmic plot (on a logarithmic scale to base 10), the particle diameter (the particle dimension) in μm, and the ordinate value on the distribution curve corresponding to a particular particle diameter on the abscissa shows the X % of the total particle volume which consists of particles having this particle dimension. In FIG. 4b, the abscissa, again in a logarithmic plot (on a logarithmic scale to base 10), shows the particle diameter (the particle dimension) in μm. The ordinate here, however, shows the proportion by volume of the total particle volume that has the particular diameter or a smaller diameter. The analysis method which forms the basis of the particle diameter distribution of FIGS. 4a and 4b is laser diffraction, which has already been detailed in this document.

Table 2 below shows the values of $d_{10}$, $d_{50}$ and $d_{90}$ (in µm) for the spray powder as a function of the dispersion pressure employed in each case.

TABLE 2

| Dispersion pressure [bar abs.] | $d_{10}$ [um] | $d_{50}$ [um] | $d_{90}$ [um] |
|---|---|---|---|
| 1.1 | 5.89 | 22.66 | 64.43 |
| 2.0 | 2.89 | 12.62 | 53.24 |
| 4.5 | 1.58 | 7.89 | 40.74 |

To an initial charge of 1000 g of the resulting spray powder cooled to 25° C. (the (residual) water content of which was 4.2% by weight) in a Werner & Pfleiderer ZS1-80 kneader were added 150 g of the $MoO_3$ ground in the production of the comparative eggshell catalyst CE (see A) of this document). With addition of 170 g of water and 200 g of a 50% by weight aqueous acetic acid solution, both of which had a temperature of 25° C., the solids mixture was kneaded in the kneader (kneading time: 2 hours; kneading temperature: 30 to 35° C.).

Subsequently, the kneaded material was extruded to circular cylindrical extrudates (length: 20 to 30 cm, diameter: 6 mm) (in principle, the aforementioned kneading and the extrusion can also be performed in a single apparatus, called a kneader/extruder (VI U 2.5/IV model from AMK (Aachener Misch-u. Knetmaschinen-Fabrik Peter Küpper GmbH & Co. KG, D-52074 Aachen)); on the industrial scale, an AMK VI U-160 kneader/extruder would be used here (machinery No. C12566)) and these were dried in a bed with a layer thickness of 2 cm (on a perforated metal sheet positioned in the center of the drying cabinet (the hole diameter of the passage orifices distributed homogeneously over the perforated metal sheet=0.5 cm; the orifice ratio of the perforated metal sheet was 60%; the total cross-sectional area of the perforated metal sheet was 35 cm×26 cm=910 $cm^2$)) for 16 h in a circulating air drying cabinet (UT 6 from Heraeus) (capacity=57 l; air flow rate=2850 l/h; the temperature in the drying cabinet (including the air temperature) was 110° C.). The residual water content of the dried extrudates was (based on the weight thereof) 1.85% by weight; the calcination weight loss of the dried extrudates was (based on the weight thereof) 20.56% by weight.

The further thermal treatment of the dried geometric shaped precursor bodies was effected in a corresponding manner, as detailed in comparative example 1A of WO 2011/134932 A1 on pages 7 and 8.

Figure 6:
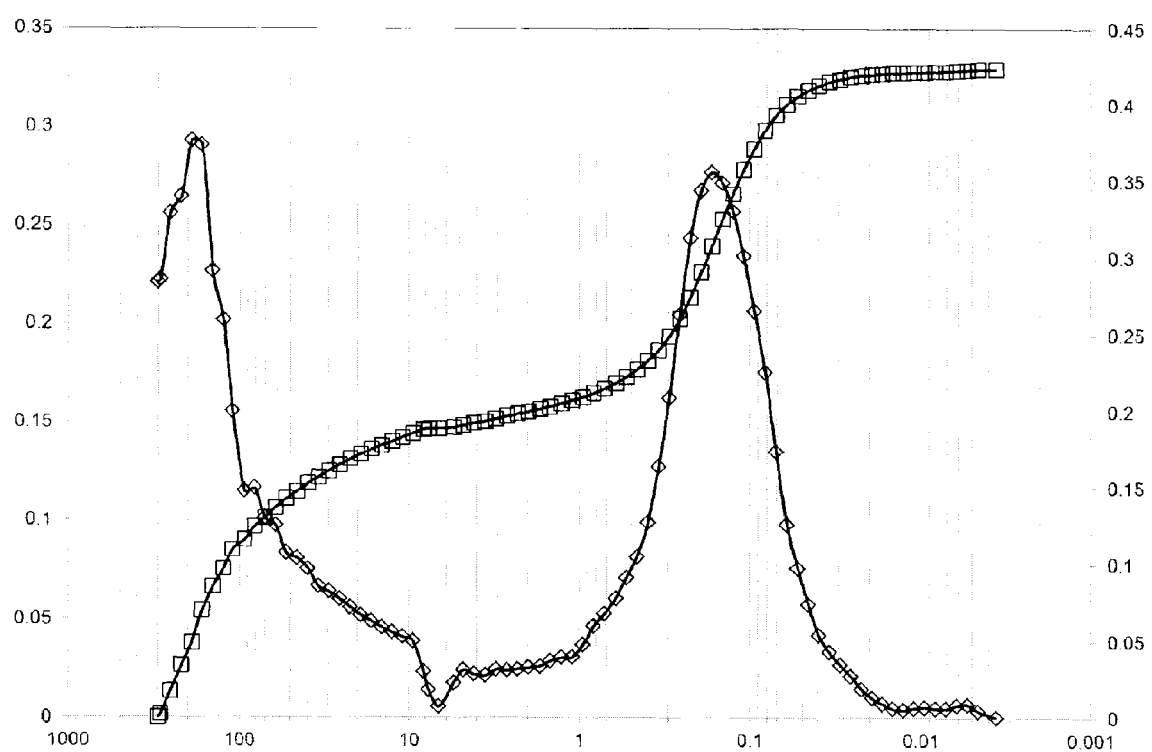
FIG. 6 shows a pore diameter distribution of the pores of the active composition powder.

The geometric shaped catalyst bodies removed from the rotary oven were subsequently, as described on page 8 of WO 2011/134932 A1, ground to a finely divided (active composition) powder (the specific BET surface area of the active composition powder was 17 $m^2/g$; the specific internal total pore surface area of the active composition powder was 8.65 $m^2/g$; the specific internal total pore volume of the active composition powder (the total intrusion volume) was 0.42 ml/g; FIG. 6 of the present document shows the pore diameter distribution of the pores of the active composition powder; on the abscissa is plotted the respective pore diameter in µm (logarithmic plot to base 10); on the left-hand ordinate is plotted the logarithm (to base 10) of the differential contribution in ([ml]/[g of active composition powder]) of the respective pore diameter to the specific (based here on the composition of the active composition powder) total pore volume ($\diamond$ curve); the maximum indicates the pore diameter having the greatest contribution to the (specific) total pore volume; on the right-hand ordinate is plotted, in ([ml]/[g of active composition powder]), the integral over the individual contributions of each of the pore diameters to the aforementioned specific total pore volume (the cumulative contribution to the aforementioned specific total pore volume) ($\square$ curve); the end point is the (specific) total pore volume based on the composition of the active composition powder (total intrusion volume)), and this was used as described on pages 8/9 of WO 2011/134932 A1 to produce an inventive annular eggshell catalyst IE (same geometric shaped support body as in the production of the annular comparative eggshell catalyst CE in A) of this document).

The inventive annular eggshell catalysts IE removed from the air circulation drying cabinet (UM 400 from Memmert GmbH+Co. KG in DE 91126 Schwabach; capacity=53 l; air flow rate=800 l (STP)/h; the temperature in the air circulation drying cabinet (including the air temperature) was 300° C. during the drying operation; the drying material was on a perforated metal sheet positioned in the center of the drying cabinet during the drying (the hole diameter of the passage orifices distributed homogeneously over the perforated metal sheet=0.5 cm; the orifice ratio of the perforated metal sheet was 60%; the total cross-sectional area of the perforated metal sheet was 35 cm×26 cm=910 $cm^2$) in the form of a bed (layer height=2 cm)) had, based on the total mass thereof, an oxidic shell fraction of 22.8% by weight. The specific BET surface area of the eggshell catalysts IE was 3.9 $m^2/g$.

Thus, the specific BET surface area Y of the active composition shell of the inventive eggshell catalysts IE is calculated from $$0.228\ m^2/g \times Y\ m^2/g + 0.772 \times 0.04\ m^2/g = 3.9\ m^2/g$$

to be Y=17 $m^2/g$.

Studies of the pore properties of the active composition shell of the inventive eggshell catalysts IE gave the following results:

The specific internal total pore surface area of the pores studied in the active composition shell of the inventive eggshell catalysts IE was 7.41 $m^2/g$.

The corresponding specific total pore volume was 0.27 ml/g.

Figure 7:
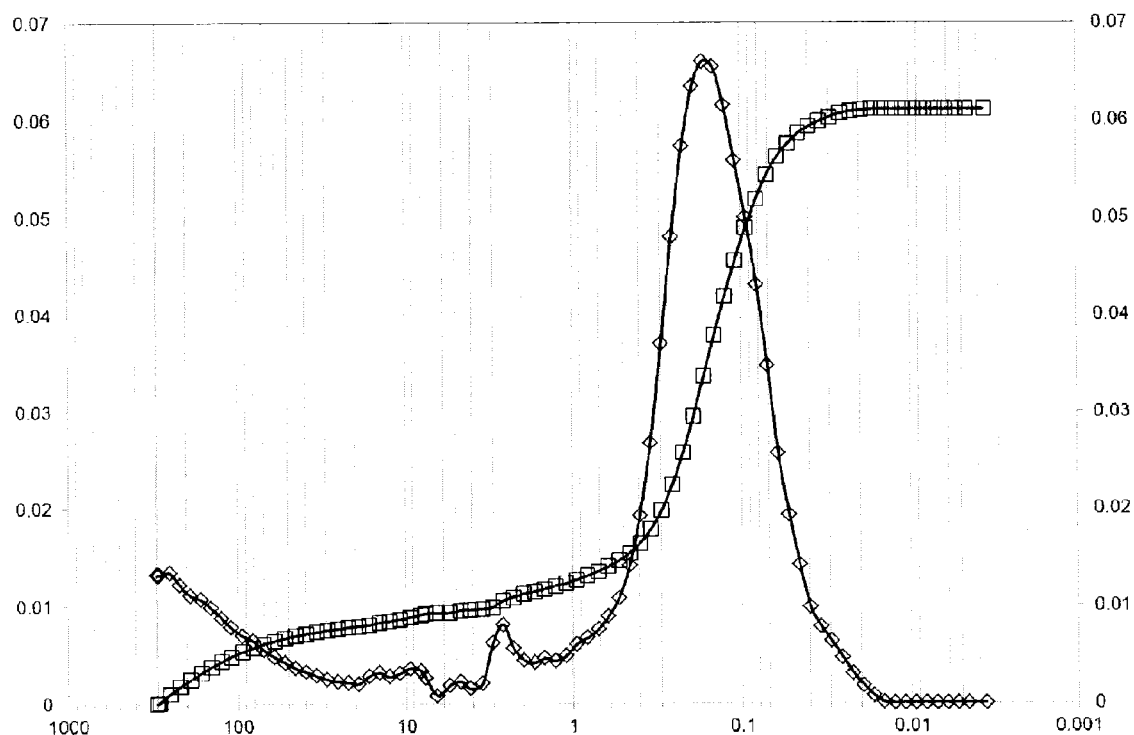
FIG. 7 shows a pore diameter distribution of the pores of the active composition shell of the inventive eggshell catalysts IE.

FIG. 7 of the present document shows the pore diameter distribution of the pores of the active composition shell of the inventive eggshell catalysts IE. On the abscissa is plotted the respective pore diameter in µm (logarithmic plot to base 10). On the left-hand ordinate is plotted the logarithm (to base 10) of the differential contribution in ([ml]/[g of eggshell catalyst]) of the respective pore diameter to the specific (based here on the overall composition formed from the composition of the geometric shaped support body and of the composition of the active composition shell) total pore volume ($\diamond$ curve). The maximum indicates the pore diameter having the greatest contribution to the (specific) total pore volume. On the right-hand ordinate is plotted, in ([ml]/[g of eggshell catalyst]), the integral over the individual contributions of each of the pore diameters to the aforementioned specific total pore volume (the cumulative contribution to the aforementioned specific total pore volume) ($\square$ curve). The end point is the (specific) total pore volume based on the overall composition of geometric shaped support body and active composition (total intrusion volume). Division of this value by 0.228 results in the specific total pore volume based on the active composition.

Figure 3A:
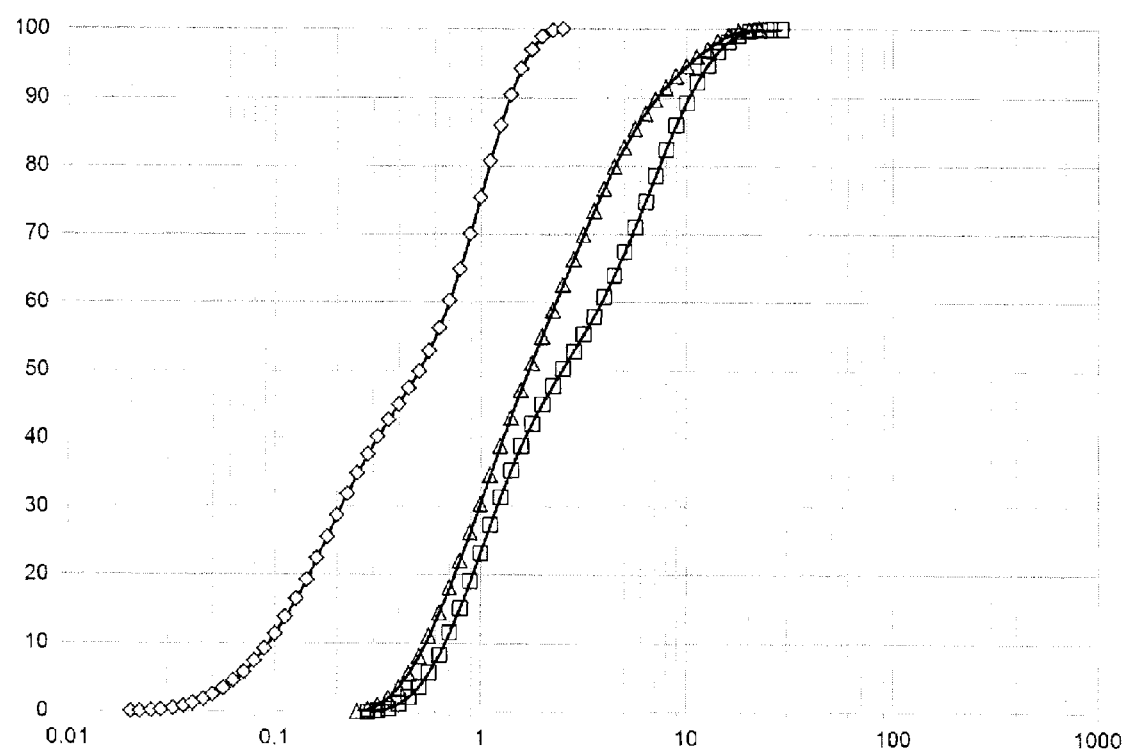
FIGS. 3a and 3b show size distributions of the particles of catalytically active multielement oxide composition powder as a function of the dispersion pressure of the compressed air used for dry dispersion.
Figure 3B:
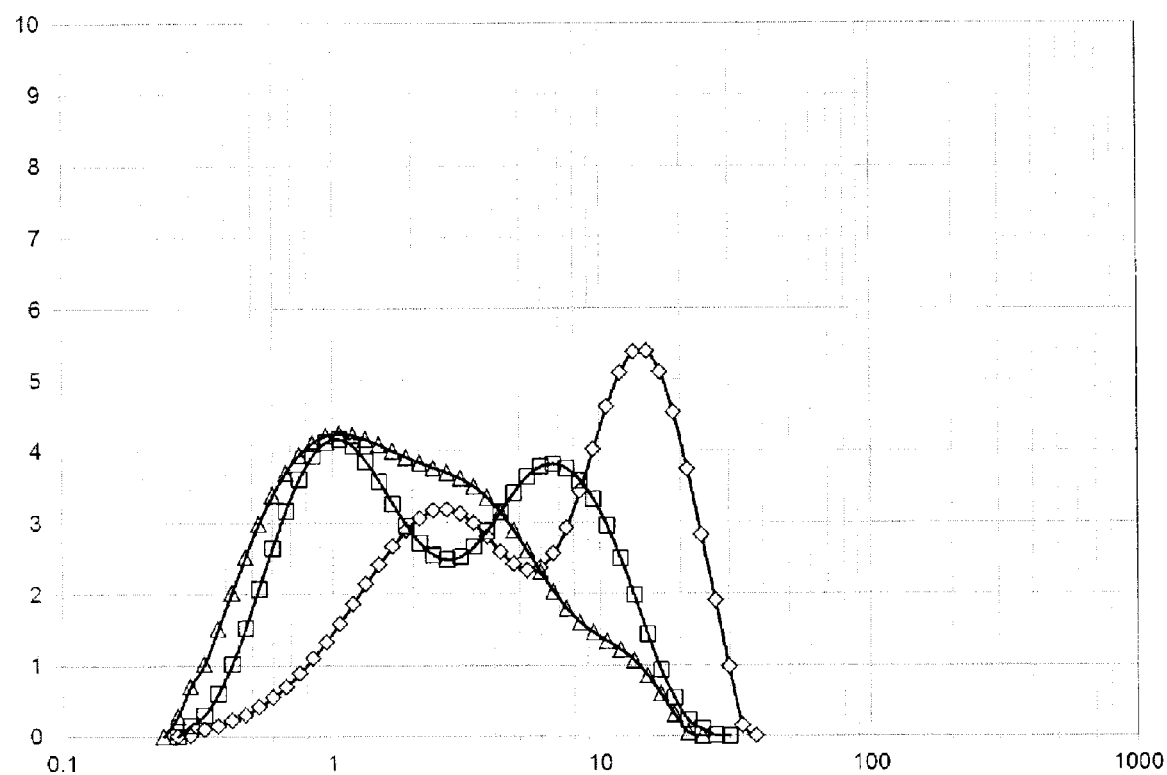

If the eggshell catalyst was produced using exclusively the ground active composition powder of the stoichiometry $Mo_{12}V_3W_{1.2}Cu_{1.2}O_x$ with its particle size distribution shown in FIGS. 3a and 3b of the present document and the rest of the procedure was as described in A) of the present document for production of the comparative eggshell catalyst CE, the result was annular comparative eggshell catalysts having an oxidic active composition content of 22.3% by weight (these can, in a corresponding manner, as described in this document for inventive eggshell catalysts IE, also be used for catalysis of the heterogeneously catalyzed partial oxidation of acrolein to acrylic acid). Studies of the pore properties of the active composition shell of these comparative eggshell catalysts gave the following results:

The specific internal total pore surface area of the pores studied in the active composition shell of these comparative eggshell catalysts was 5.88 m²/g.

The corresponding specific total pore volume was 0.20 ml/g.

Figure 8:
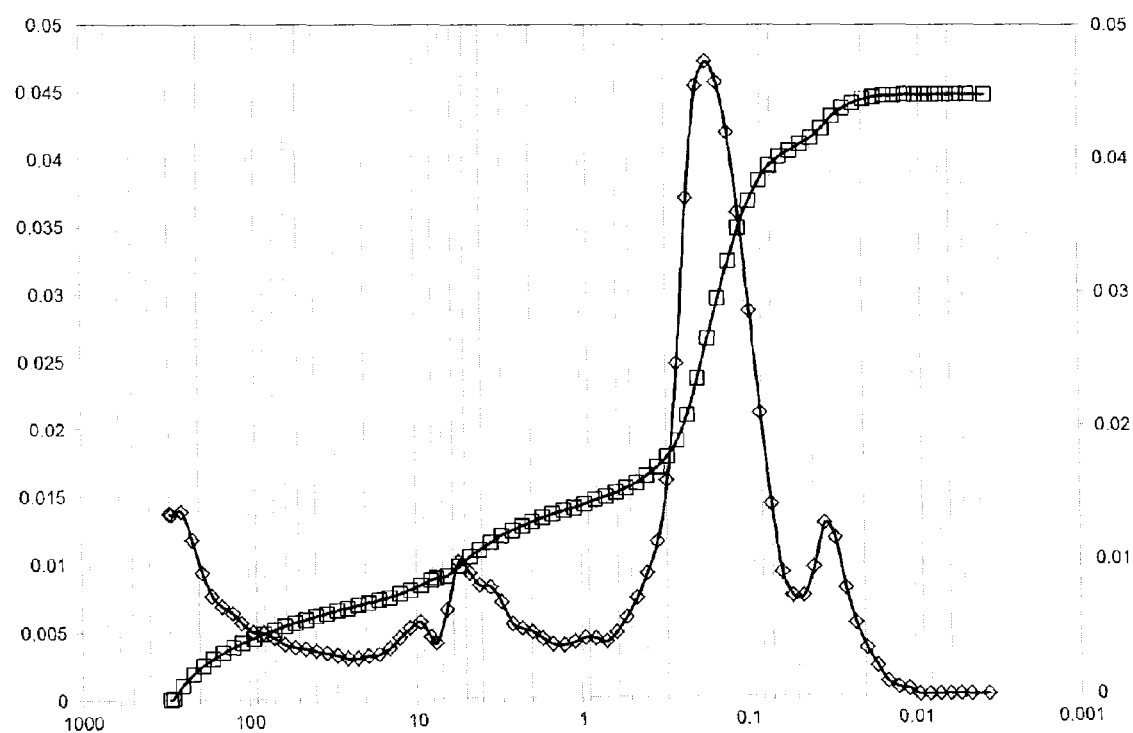
FIG. 8 shows a pore diameter distribution of the pores of the active composition shell of these comparative catalysts.

FIG. 8 of the present document shows the pore diameter distribution of the pores of the active composition shell of these comparative catalysts. On the abscissa is plotted the respective pore diameter in μm (logarithmic plot to base 10). On the left-hand ordinate is plotted the logarithm (to base 10) of the differential contribution in ([ml]/[g of eggshell catalyst]) of the respective pore diameter to the specific (based here on the overall composition formed from the composition of the geometric shaped support body and of the composition of the active composition shell) total pore volume ($\diamond$ curve). The maximum indicates the pore diameter having the greatest contribution to the (specific) total pore volume. On the right-hand ordinate is plotted, in ([ml]/[g of eggshell catalyst]), the integral over the individual contributions of each of the pore diameters to the aforementioned specific total pore volume (the cumulative contribution to the aforementioned specific total pore volume) ($\square$ curve). The end point is the (specific) total pore volume based on the overall composition of geometric shaped support body and active composition (total intrusion volume). Division of this value by 0.223 results in the specific total pore volume based on the active composition.

C) Testing of the Eggshell Catalysts CE and IE as Catalysts for the Heterogeneously Catalyzed Partial Gas Phase Oxidation of Acrolein to Acrylic Acid A reaction tube (V2A steel; external diameter 30 mm; wall thickness 2 mm; internal diameter 26 mm; length 464 cm) was charged from the top downward as follows:

Section 1: length 79 cm
    empty tube;
Section 2: length 62 cm
    preliminary bed of steatite rings of geometry 7 mm×3 mm×4 mm (external diameter×length×internal diameter; C220 steatite from CeramTec);
Section 3: length 100 cm
    fixed catalyst bed composed of a homogeneous mixture consisting of 20% by weight of steatite rings of geometry 7 mm×3 mm×4 mm (external diameter×length× internal diameter); C220 steatite from CeramTec) and 80% by weight of the respective eggshell catalyst;
Section 4: length 200 cm
    fixed catalyst bed consisting exclusively of the eggshell catalyst used in the respective section 3;
Section 5: length 10 cm
    downstream bed of the same steatite rings as in section 2;
Section 6: length 14 cm
    catalyst base made of V2A steel to accommodate the fixed catalyst bed.

A reaction gas mixture conducted through the respective reaction tube charged as described above, flowing through the reaction tube from the top downward, had the following contents:

4.3% by vol. of acrolein,
0.2% by vol. of propene,
0.2% by vol. of propane,
0.3% by vol. of acrylic acid,
5.4% by vol. of $O_2$,
7% by vol. of $H_2O$,
0.4% by vol. of CO and $CO_2$, and
82.2% by vol. of $N_2$.

The space velocity of acrolein on the fixed catalyst bed (as defined in the present document) was in each case 75 l (STP)/ l·h. The reaction gas mixture was supplied to the reaction tube at a temperature of 255° C. The working pressure at the inlet into the reaction tube was 1.6 bar (abs.).

Over the length of the reaction tube (apart from the last 10 cm of the empty tube in section 1 and the last 3 cm of the tube in section 6), a stirred and externally electrically heated salt bath (mixture of 53% by weight of potassium nitrate, 40% by weight of sodium nitrite and 7% by weight of sodium nitrate; 50 kg of salt melt) flowed around the reaction tube (the flow rate at the tube was 3 m/s (in the plane at right angles to the longitudinal axis of the tube)).

Viewed over the tube length, the salt bath flowed at a flow rate of 3 m/s, in the opposite direction to the reaction gas mixture.

The salt bath temperature $T^B$ (° C.) (with which the salt bath was supplied) was set in all cases so as to result in an acrolein conversion C of 99.3 mol % based on a single pass of the reaction gas mixture through the fixed catalyst bed. Along the reaction tube, there was no change in the salt bath temperature owing to additional heating (the salt bath emitted more heat than was released by the reaction tube to the salt bath). The feed temperature of the reaction gas mixture (at the inlet into the reaction tube) was set to the respective salt bath temperature in each case.

Table 3 below shows the results as a function of the eggshell catalyst used after 100 hours of operation in each case, S being the selectivity of acrylic acid formation.

TABLE 3

| Eggshell catalyst | $T^B$ [° C.] | C [mol %] | S [mol %] |
|---|---|---|---|
| CE | 261 | 99.3 | 96.7 |
| IE | 248 | 99.3 | 97.3 |

Both in the case of use of the eggshell catalyst CE and in the case of use of the eggshell catalyst IE, no increase in the salt bath temperature was required to maintain the target conversion over an operating period of 55 days. The selectivity of acrylic acid formation was stable over the entire operating period in both cases.

The results shown in the table indicate that, in the case of inventive incorporation of $MoO_3$ into the catalytically active composition, the result is not only fully satisfactory long-term performance thereof but additionally both a higher activity and a higher selectivity of target product formation.

Both the eggshell catalysts CE and the eggshell catalysts IE were storable at temperatures of 20 to 40° C. under ambient air having up to 90% or higher relative air humidity without losing catalytic activity.

U.S. Provisional Patent Application No. 61/761,812, filed Feb. 7, 2013, is incorporated into the present patent application by literature reference.

With regard to the abovementioned teachings, numerous changes and deviations from the present invention are possible. It can therefore be assumed that the invention, within the scope of the appended claims, can be performed differently than the way described specifically herein.

The invention claimed is:

1. A process for producing a catalytically active composition, the process comprising:
using sources of elemental constituents of a multielement oxide comprising Mo and V to obtain an aqueous solution, or to obtain an aqueous suspension with the proviso that each of the sources passes through the state of an aqueous solution,
spray drying the aqueous solution or aqueous suspension to obtain a spray powder,
adding at least one pulverulent oxide of molybdenum and optionally one or more shaping assistants into the spray powder, thereby obtaining a mixture,
homogeneously mixing and shaping the mixture, thereby obtaining geometric shaped precursor bodies, and
thermally treating the geometric shaped precursor bodies, thereby obtaining the catalytically active composition comprising the at least one pulverulent oxide of molybdenum and the multielement oxide.

2. The process according to claim 1, wherein the at least one pulverulent oxide of molybdenum is molybdenum dioxide, molybdenum trioxide or a mixture of molybdenum dioxide and molybdenum trioxide.

3. The process according to claim 1, wherein the at least one pulverulent oxide of molybdenum has a specific surface area $O_M$ of $\leq 20$ m$^2$/g.

4. The process according to claim 1, wherein the at least one pulverulent oxide of molybdenum has a specific surface area $O_M$ of $\geq 0.01$ m$^2$/g.

5. The process according to claim 1, wherein the at least one pulverulent oxide of molybdenum has a particle diameter $d_{90}$ of $\leq 20$ μm.

6. The process according to claim 1, wherein the at least one pulverulent oxide of molybdenum has a particle diameter $d_{10}$ of $\geq 50$ nm.

7. The process according to claim 1, wherein the at least one pulverulent oxide of molybdenum, based on a total weight of the catalytically active composition, is added in an amount of >0 and ≤50% by weight.

8. The process according to claim 1, wherein a molar proportion of element Mo in a total amount of elements other than oxygen in the multielement oxide is from 5 to 95 mol %.

9. The process according to claim 1, wherein a molar ratio of Mo/V in the multielement oxide is from 15:1 to 1:1.

10. The process according to claim 1, wherein the multielement oxide additionally comprises Cu.

11. The process according to claim 1, wherein the multielement oxide satisfies formula (I):

$$Mo_{12}V_aX^1{}_bX^2{}_cX^3{}_dX^4{}_eX^5{}_fX^6{}_gO_n \qquad (I)$$

$X^1$ is at least one of W, Nb, Ta, Cr and Ce,
$X^2$ is at least one of Cu, Ni, Co, Fe, Mn and Zn,
$X^3$ is at least one of Sb and Bi,
$X^4$ is at least one of Li, Na, K, Rb, Cs and H,
$X^5$ is at least one of Mg, Ca, Sr, and Ba,
$X^6$ is at least one of Si, Al, Ti and Zr,
a is a number of from 1 to 6,
b is a number of from 0.2 to 4,
c is a number of from 0 to 18,
d is a number of from 0 to 40,
e is a number of from 0 to 2,
f is a number of from 0 to 4,
g is a number of from 0 to 40, and
n is a number determined by valency and frequency of elements in the formula (I) other than oxygen.

12. The process according to claim 1, wherein The multielement oxide satisfies formula (II):

$$Mo_{12}V_aX^1{}_bX^2{}_cX^5{}_fX^6{}_gO_n \qquad (II)$$

$X^1$ is at least one of W and Nb,
$X^2$ is at least one of Cu and Ni,
$X^5$ is at least one of Co and Sr,
$X^6$ is at least one of Si and Al,
a is a number of from 3 to 4.5,
b is a number of from 1 to 1.5,
c is a number of from 0.75 to 2.5,
f is a number of from 0 to 0.5,
g is a number of from 0 to 8, and
n is a number determined by valency and frequency of elements in the formula (II) other than oxygen.

13. The process according to claim 1, wherein said thermally treating comprises calcinating at 200 to 600° C.

14. The process according to claim 13, wherein Said calcinating extends over a period of from 0.5 h to 24 h.

15. The process according to claim 1, further comprising:
converting the catalytically active composition to a finely divided form, and
applying the finely divided form as a shell of the catalytically active composition to an outer surface of a geometric shaped support body.

16. The process according to claim 15, wherein the shell of the catalytically active composition has a thickness of from 10 to 1000 μm.

17. The process according to claim 1, wherein said shaping occurs in such a way that a shell of the mixture is applied directly to an outer surface of a geometric shaped support body.

18. A catalyst obtained by the process according to claim 1.

19. A catalyst, consisting of:
a geometric shaped support body,
a catalytically active composition applied to an outer surface of a geometric shaped support body, and
optionally a binder,
wherein the catalytically active composition is obtained by the process according to claim 1.

20. A catalyst, consisting of:
a geometric shaped support body,
a catalytically active composition present on an outer surface of a geometric shaped support body, and
optionally a binder,
wherein the catalytically active composition is obtained by the process according to claim 1.

21. A process, comprising:
oxidizing (meth)acrolein to (meth)acrylic acid in the presence of a catalyst via a heterogeneously catalyzed partial gas phase oxidation,
wherein the catalyst is at least one catalyst according to claim 18.

22. The process according to claim 21, wherein the catalyst is part of a fixed catalyst bed with a (meth)acrolein space velocity of from 50 l (STP)/l·h to 250 l (STP)/l·h.

* * * * *